US012691142B2

(12) United States Patent
Suñé Negre et al.

(10) Patent No.: US 12,691,142 B2
(45) Date of Patent: Jul. 28, 2026

(54) ESSENTIALLY SODIUM-FREE EFFERVESCENT SOLID PHARMACEUTICAL COMPOSITIONS

(71) Applicant: INTAS PHARMACEUTICALS LTD., Ahmedabad (IN)

(72) Inventors: José María Suñé Negre, Barcelona (ES); Manuel Roig Carreras, Calafell Platja (ES); Marc Suñé Pou, Barcelona (ES); Anna Nardi Ricart, Barcelona (ES); Xavier Formosa Márquez, Sant Quirze del Vallès (ES); Manishkumar Jayantibhai Chauhan, Ahmedabad (IN); Venkataramana Naidu, Ahmedabad (IN); Manish Mavjibhai Patel, Ahmedabad (IN)

(73) Assignee: Intas Pharmaceuticals Limited, Ahmedabad (IN)

( * ) Notice: Subject to any disclaimer, the term of this patent is extended or adjusted under 35 U.S.C. 154(b) by 623 days.

(21) Appl. No.: 17/707,425

(22) Filed: Mar. 29, 2022

(65) Prior Publication Data

US 2022/0226368 A1     Jul. 21, 2022

Related U.S. Application Data

(63) Continuation of application No. PCT/IB2020/059214, filed on Oct. 1, 2020.

(30) Foreign Application Priority Data

Oct. 2, 2019     (EP) .................................... 19382846

(51) Int. Cl.
*A61K 33/10* (2006.01)
*A61K 9/46* (2006.01)

(52) U.S. Cl.
CPC ............ *A61K 33/10* (2013.01); *A61K 9/0007* (2013.01)

(58) Field of Classification Search
CPC .............................. A61K 33/10; A61K 9/0007
See application file for complete search history.

(56) References Cited

U.S. PATENT DOCUMENTS 6,242,002 B1     6/2001   Tritthart et al.
6,245,353 B1 *   6/2001   Tritthart .................. A61P 37/08
                                                514/784

2008/0287456 A1* 11/2008 Roberts ................... A61P 27/16
                                                514/769
2011/0014132 A1     1/2011  Liu
2016/0058700 A1*   3/2016  Laza-Knoerr ........ A61K 9/2009
                                                264/122

FOREIGN PATENT DOCUMENTS

| CN | 104248626 | A | * | 12/2014 |
|---|---|---|---|---|
| CN | 104248626 | B | | 12/2016 |
| DE | 198 14 257 | | | 10/1999 |
| EP | 1 067 904 | | | 12/2001 |
| EP | 1 837 019 | | | 9/2007 |
| FR | 2 787 715 | | | 6/2000 |
| WO | 00/28973 | | | 5/2000 |
| WO | 2011/136751 | | | 11/2011 |
| WO | 2015/040460 | | | 3/2015 |
| WO | 2016/131947 | | | 8/2016 |

OTHER PUBLICATIONS

English translation of CN 104248626 (A) provided by EPO (Year: 2024).*
International Search Report issued in International Application No. PCT/IB2020/059214, Feb. 10, 2021, 4 pages.
Written Opinion issued in International Application No. PCT/IB2020/059214, Feb. 10, 2021, 8 pages.
Committee for Human Medicinal Products (CHMP), "Questions and answers on sodium used as an excipient in medicinal products for human use", European Medicines Agency—Science Medicines Health, Oct. 9, 2017, EMA/CHMP/338679/2014, 11 pages.
George, et al., "Association between cardiovascular events and sodium-containing effervescent, dispersible, and soluble drugs: nested case-control study", BMJ, 347:f6954, Nov. 26, 2013, 8 pages.
Meier, et al., "Antiepileptics and bone health", Therapeutic Advances in Musculoskeletal Disease, 3(5), 2011, pp. 235-243.

* cited by examiner

*Primary Examiner* — Michael P Cohen
(74) *Attorney, Agent, or Firm* — HSML P.C.

(57)     ABSTRACT

Essentially sodium-free effervescent solid pharmaceutical compositions The present invention relates to an effervescent solid pharmaceutical composition, which is essentially free of sodium content, comprising: a therapeutically effective amount of an active pharmaceutical ingredient; one or more pharmaceutically acceptable alkaline earth metal carbonates or hydrogencarbonates in an amount from 1 to 31% by weight of the composition; and one or more pharmaceutically acceptable acids, pharmaceutically acceptable acid salts, or alternatively, a mixture thereof, in an amount from 2 to 62% by weight of the composition; together with one or more pharmaceutically acceptable excipients or carriers; wherein, the total content of the ion sodium in the effervescent solid pharmaceutical composition is equal to or lower than 1 mmol. It also relates to processes for its preparation and its use in therapy.

10 Claims, No Drawings

ESSENTIALLY SODIUM-FREE EFFERVESCENT SOLID PHARMACEUTICAL COMPOSITIONS

This application claims the benefit of European Patent Application 19382846.4 filed Oct. 2, 2019.

The present invention relates to the field of pharmacy. Particularly, to an effervescent solid pharmaceutical composition which is essentially free of sodium and which has a fast disintegration upon contact with water before its administration. It also relates to processes for its preparation and its use in therapy.

BACKGROUND ART

Tablets and capsules are the preferred pharmaceutical forms for the administration of drugs because they are precisely dosed, easily produced on a large scale and contribute to a good compliance with treatment. However, some patients may have trouble in swallowing tablets or capsules. Such condition is particularly important amongst elderly, stroke victims, children, patients affected by psychiatric disorders who refuse to swallow or in general, people who suffer from dysphagia for any other reason.

Liquid dosage forms such as oral solutions, suspensions or syrups constitute alternatives for those patients having trouble in swallowing. However, these dosage forms provide a less precise control of the dose since they need to be manipulated by the patient or caregiver; they are more difficult to be transported, and more prone to be contaminated and spoilt, due to the lack of unit-dose packaging.

In this context, effervescent solid compositions represent an excellent solution for patients suffering from difficulties in swallowing. They allow a precise control of the dose and can be packaged in unit doses, facilitating their transportation and improving adherence of the patients to the treatment. In particular, effervescent solid compositions have a fast disintegration and can also have a fast dissolution time upon contact with a small amount of water to yield a suspension or a solution respectively before their administration. In particular, the effervescent solid pharmaceutical compositions disintegrate fast in contact with water thanks to the release of $CO_2$ gas to yield liquid suspensions or solutions that can be swallowed easier than entire tablets or capsules. The effervescence can be achieved using an effervescent acid-base couple (or pair), which produces gas when carbonate ions (base) become protonated in acidic aqueous environments. Therefore, effervescent systems depend on the reaction between an acid (or any other constituent that creates an acidic environment) and a carbonate or bicarbonate.

Sodium carbonate and sodium bicarbonate are the preferred $CO_2$ sources in effervescent systems due to their high solubility in water and their good palatability. Unfortunately, these products tend to deliver significant amounts of sodium along with the active pharmaceutical ingredient. Guidance from organisations such as the World Health Organisation (WHO) and the US Food and Drug Administration (FDA) suggest decreasing sodium intake in general, and particularly in population suffering from hypertension and other cardiovascular diseases.

Besides, the European Medicines Agency (EMA) has recently paid attention to sodium used as an excipient in medicinal products for human use (EMA/CHMP/338679/2014). In this document EMA says that most medicines that contain high levels of sodium are likely to be effervescent or soluble. EMA warns that a study in 1,292,337 patients over the age of 18 recently reported that the high sodium content of some effervescent, soluble and dispersible medicines might be associated with an increased risk of cardiovascular disease (George, J. et al. The Association of Cardiovascular Events with Sodium-Containing Effervescent, Dispersible and Soluble Medications; Nested Case-control Study, BMJ, 2013; 347: f6954).

The WHO recommends adults to consume less than 2 g (or 87 mmol) sodium per day. Effervescent tablets disclosed in the state of the art usually contain exceedingly high levels of sodium, even representing 25% of the WHO recommended maximum daily amount for dietary sodium. Then, there is a need of providing effervescent solid pharmaceutical compositions delivering a low content of ion sodium or even being essentially free of sodium. This is particularly important for medications which should be administered chronically, since the cumulative amount of sodium delivered by conventional effervescent solid formulations is unacceptably high for patients with cardiovascular diseases or on low sodium diets.

Different approaches have been proposed to reduce or eliminate the ion sodium content of pharmaceutical effervescent solid compositions such as effervescent tablets. One approach as shown by WO2015/040460 has been replacing partially or totally sodium carbonate or sodium bicarbonate salts by the equivalent amount of potassium carbonate or potassium bicarbonate salts. However, potassium salts are in general less stable than sodium salts, for example potassium bicarbonate decomposes at lower temperatures (between 100 and 200° C.) than sodium bicarbonate (about 270° C.). Therefore, potassium salts have an inherent tendency to be metastable and high reactive. Consequently, the use of potassium salts may require special packaging to deal with corrosion and extraordinary precautions of the equipment used. Therefore, effervescent solid pharmaceutical compositions based on potassium carbonate sources can be difficult to prepare, making them less cost-effective, especially at industrial scale. Furthermore, it is also disclosed in the state of the art that an excessive dietary intake of potassium could also lead to hyperkalaemia, a condition including symptoms such as muscle weakness, fatigue and arrhythmia among others. In addition, potassium containing compositions exhibit a metallic and bitter taste which is difficult to mask.

Carbonates of alkaline earth metals have been proposed by some authors as potential substitutes of sodium and potassium carbonates for effervescent solid pharmaceutical compositions to overcome the previous concerns and at the same time to be cost-effective at industrial scale.

Alkaline earth metals, such as calcium and magnesium, are nutrients that the body needs to stay healthy. In one hand, the body needs calcium to maintain strong bones to carry out many important functions such as for example to move muscles and for nerves to carry messages between the brain and every body part. In addition, calcium is used to help blood vessels move blood throughout the body and to help release hormones and enzymes that affect almost every function in the human body. However, getting to much calcium can be harmful causing constipation and might also interfere with the body's ability to absorb iron and zinc. In adults, too much calcium might increase the risk of kidney stones. Some studies show that people who consume high amounts of calcium might have increased risks of prostate cancer and heart disease. Further, calcium can interact or interfere with certain medicines, and some medicines can lower or raise calcium levels in the body. For example, calcium can reduce the absorption of some drugs (such as bisphosphonates and antibiotics) when taken together. Otherwise, thiazide-type diuretics (such as Diuril® and Lozol®) reduce calcium excretion by the kidneys.

In the other hand, magnesium is also important for many processes in the body, including regulating muscle and nerve function, blood sugar levels, blood pressure and making protein, bone, and DNA. In healthy people, the kidneys can get rid of any excess of magnesium in the urine and then, the magnesium intake in healthy people does not need to be limited. However, high intakes of magnesium can cause diarrhea, nausea, and abdominal cramping; and extremely high intakes of magnesium can lead to irregular heartbeat and cardiac arrest. Further, magnesium can also interact or interfere with some medicines such as Bisphosphonates and antibiotics.

Most people do not get amounts of calcium and/or magnesium above the upper limits from food alone; excess intakes usually come from the use of supplements and medications. In particular, surveys show that some older women probably get amounts somewhat above the upper limit since the use of calcium/magnesium-containing supplements and drugs is common among these women.

Therefore, the Office of Dietary Supplement of the National Institutes of Health of the U.S. Department of Health and Human Services stablished the average daily recommended amounts of calcium and magnesium that a person (depending on the age) need each day, and also the daily upper limits in milligrams. For example, the calcium daily upper limits for children from 9-18 years is 3 g; for adults from 19-510 years is 2.5 g and for adults older than 51 years is 2 g. In the case of magnesium, the upper limits include only magnesium from dietary supplements and medications (but not magnesium found naturally in food). For example, the magnesium daily upper limit for children from 9-18 years and adults is 350 mg. Besides, carbonates of alkaline earth metals such as calcium carbonate or magnesium carbonate are sparingly soluble in water and thus, the fast disintegration by effervescence reaction is severely hindered. Therefore, effervescent compositions comprising alkaline earth metal carbonates are not usually quickly dissolved and as a result, the achieved water mixture after the disintegration of the effervescent composition is neither transparent nor clear leaving residues and/or foams which hinders the bio-absorption of the active ingredient. Furthermore, the taste of the solutions yielded by these compositions in water is unpleasant, thereby compromising the adherence to treatment. For these reasons, obtaining effervescent solid pharmaceutical compositions based on alkaline earth metal carbonates or bicarbonates which have a fast disintegration and yield transparent and palatable aqueous solutions is still a challenge. Even more difficult, having a low amount of alkaline earth metals for avoiding the heathy risks associated to their high intake.

Manufacturing of effervescent tablets requires the control of some critical steps and conditions. Low relative humidity and moderate-to-cool temperatures are essential to prevent the dissolution of the effervescing agents and to avoid the effervescence reaction taking place during the manufacturing process. Therefore, dry methods such as dry granulation or direct compression are the preferred methods of producing effervescent solid compositions because no liquids are involved. When wet granulation processes are needed, non-aqueous solvents such as ethanol or isopropanol could be used. On the other hand, if water is to be used as solvent, two separate granulation steps should be carried out, i.e. one for the alkaline and one for the acid components, with a subsequent dry blending step. In this context, the advantages of dry methods are evident, since these allow avoiding the use of organic solvents, reduce the number of process step, and lead to a more environment-friendly and cost-effective manufacturing process.

European patent application EP1837019 A1 discloses oral pharmaceutical compositions in the form of orally dispersible tablets containing calcium carbonate and optionally vitamin D and/or fluorine for the treatment or prevention of osteoporosis. Formulations disclosed in this document were obtained following dry methods such as rotary compression and direct compression (cf. paragraphs [0086] to [0090]). On the other hand, the orally dispersible tablets disclosed in EP1837019 comprise a high percentage of the effervescent couple (i.e. from about 81% to about 94% w/w), and more specifically a high percentage of calcium carbonate (i.e. from about 65% to about 80% w/w), which is disadvantageous because they are extremely abrasive and tend to damage the tabletting tools, thereby causing a severe economic impact in the manufacturing process.

PCT patent application WO00/28973 discloses processes for the manufacture of orally administrable pharmaceutical compositions in tablet form containing a physiologically tolerable calcium compound, such as for example calcium carbonate. In this context, example 6 discloses effervescent tablets comprising calcium carbonate, citric acid and vitamin D3 together with other pharmaceutical excipients, wherein the effervescent couple amount is about 90% w/w and the calcium carbonate amount is about 33% w/w. Effervescent tablets as disclosed in example 6 are obtained following a process of wet granulation (as disclosed in example 1), wherein at least two separate step processes (example 2) are needed. The need of at least two granulation steps, one of them being a wet granulation process makes the effervescent tablets of WO 00/28973 more difficult to be produced, hindering at the same time the integrity of the final effervescent tablet and its effervescence time. Furthermore, as it is mentioned above, the use of high amounts of the effervescent couple and particularly of calcium carbonate are inappropriate because of its abrasiveness that damages the tabletting tools.

Finally, European patent application EP1067904 A1 discloses quick dissolving fizzy formulations for oral applications, containing cetirizine or its pharmaceutically compatible salts, a fizzy base comprising alkali or alkaline earth carbonates and other pharmaceutical excipients. Examples 6 and 7 to 9 disclose soluble granules and dispersible tablets, respectively, which comprise cetirizine as active pharmaceutical ingredient and calcium carbonate and citric acid as the effervescent couple and are obtained by separate bed process (paragraph 31). Furthermore, although examples 6 to 9 disclose formulations containing lower percentages of the effervescing couple compared to the formulations disclosed in EP 1837019 A1 and WO00/28973, the amount of calcium carbonate in the formulations of EP 1067904 is still too high (i.e. higher than 32% w/w), thereby still yielding too abrasive mixtures.

Therefore, from what is known in the art it is derived that there is a long-felt need of providing effervescent compositions that without contributing to increase the daily sodium and alkaline earth metals intake have also a fast time of effervescence that yields to palatable and transparent liquids. Furthermore, there is also the need of providing straightforward processes for the manufacture of such effervescent compositions that are easy to scale-up, environment-friendly, cost-effective, and which may avoid the use of highly abrasive mixtures such as those comprising big amounts of calcium carbonate.

SUMMARY OF THE INVENTION

The inventors of the present invention have surprisingly found a solid effervescent pharmaceutical composition which does not contribute to increase the sodium and alkaline earth metals dietary intake of the patients and at the same time, exhibits a fast effervescence time and yields to palatable and residue-less liquids.

Compositions of the present invention are defined as "essentially sodium-free" according to the updated EMA guidelines (cf. EMA/CHMP/338679/2014). Therefore, the composition of the present invention is appropriate for children and elderly, as well as other patients that need to reduce, control or avoid the sodium intake in the diet such as for example patients suffering from hypertension or other cardiovascular diseases. Another advantage associated with the "essentially sodium-free" compositions of the present invention is that they are also appropriate for being administered chronically, because the amount of ion sodium delivered from the compositions is null or low enough, so that high cumulative levels of sodium ions cannot be achieved.

Further, the compositions of the present invention can be also defined as "low alkaline earth metal content". Therefore, the composition of the present invention is appropriate for patients that need to reduce or control the alkaline earth metal intake such as for example patients suffering from kidney diseases or disorders. Another advantage associated with the "low alkaline earth metal content" compositions of the present invention is that they are also appropriate for being administered chronically, because the amount of alkaline earth metal ion, mainly ion calcium and/or ion magnesium, delivered from the compositions is low enough from the recommended upper limits, not being a critical factor for reaching or even exceed the daily upper limit recommended.

By way of illustration, the composition of the invention comprising the highest amount of alkaline earth metal content is the composition of the invention comprising 1500 mg of levetiracetam (Example 8), which contains about 450 mg of calcium carbonate (i.e. about 180 mg of calcium ion). Therefore, the upper intake of calcium ion associated to the administration of the composition of the invention twice daily is about 360 mg/day of calcium ion, which is far from the daily upper limit (about 3000 mg/daily). In the case of magnesium, the composition of the invention comprising the 1000 mg of levetiracetam (Example 16), contains about 150 mg of magnesium carbonate (i.e. about 43 mg of magnesium ion). Therefore, the upper intake of magnesium associated to the administration of the composition of the invention twice daily is about 130 mg/day of magnesium ion, which is again far from the daily upper limit (about 3000 mg/daily).

Besides, the composition of the present invention disintegrates within 5 minutes or less upon contact with 200 mL of water R at 15-25° C., leaving no agglomerates or residues when effervescence ceases, thereby fulfilling the disintegration test established for effervescent tablets by European Pharmacopoeia (Ph.Eur). Particularly, the composition of the present invention (after disintegration) creates a palatable water solution without residues and/or foam, which provides an excellent bioavailability of the active ingredient, as well as an easy way to ingest, even for those patients who experience difficulties in swallowing conventional tablets and capsules. Besides, the pleasant taste of the water solution also improves the adherence to the treatment. Also, the composition of the present invention reduces the risk of drug-induced esophagitis, which occurs when a tablet is caught in the oesophagus, rendering the size and shape of the composition irrelevant allowing large amounts of active ingredients in a single dose.

Furthermore, without being bound to any theory, it seems that the above-mentioned palatable water solution obtained after the disintegration of the composition of the present invention also has an appropriate pH value that allows buffering the gastric pH above 3. The resultant increased gastric pH is advantageous because enhanced the gastric and oesophageal tolerability of the composition of the present invention and also the tolerability of other drugs that cause a reduction of the gastric pH after its administration (such as bisphosphonate drugs). Then, the administration of the composition of the invention reduces the risk of suffering gastric and oesophageal mucosa irritation, and therefore, the composition of the invention is even appropriate for patients suffering from dyspepsia, dysphagia and esophageal ulcers. In addition, the composition of the present invention comprises one or more alkaline earth metal carbonates or bicarbonates, particularly calcium carbonate or calcium bicarbonate, which is advantageous for people with special calcium needs such as babies, young children, adolescents, pregnant or breastfeeding women, as well as elderly people; and other people with special requirements of calcium for being at risk of developing brittle bone disease or osteoporosis; such as for example patients suffering from epilepsy and is treated with antiepileptic drugs. However, as mentioned above, the amount of the alkaline earth metal in the compositions of the invention is far remote from the daily upper recommended limit.

In the recent years, there has been increasing evidence suggesting that epilepsy and its treatment can have adverse effects on bone mineralization and calcium metabolism. Many studies have shown a significant reduction in bone mineral density and an increased fracture risk in patients treated with enzyme-inducing antiepileptics (phenobarbital, carbamazepine and phenytoin). Although data on bone-specific effects of newer antiepileptic drugs are limited, alterations of bone metabolism have been reported for oxcarbazepine, gabapentin and, in preclinical studies, for levetiracetam (Meier, C. et al. Antiepileptics and Bone Health, Ther. Adv, Musculoskelet. Dis., 2011, 3(5), pp. 235-243).

Finally, regarding the preparation process of the compositions of the invention, the low amount of acid/base couple, and particularly the low amount of one or more alkaline earth metal carbonates or bicarbonates, provides a much less abrasive blend for compression, thereby increasing the useful life of the tabletting tools. Besides, the specific combination of excipients of the composition of the present invention allows manufacturing them by dry methods, such as direct compression and dry granulation processes (such as MAGD granulation processes) with a simple, environment-friendly and cost-effective process, which may be suitable for industrial scale up. In addition, the compositions of the invention can also be manufactured by a simple wet granulation process, which implies a unique and simple wet-granulation step using an insignificant amount of granulating liquid instead of the complex processes disclosed in the state of the art which comprises at least two granulation steps.

Thus, the first aspect of the present invention relates to an effervescent solid pharmaceutical composition comprising: a therapeutically effective amount of an active pharmaceutical ingredient; one or more pharmaceutically acceptable alkaline earth metal carbonates or hydrogencarbonates in an amount from 1 to 31% by weight of the composition; and one or more pharmaceutically acceptable acids, pharmaceutically acceptable acid salts, or alternatively, a mixture thereof, in an amount from 2 to 62% by weight of the composition; together with one or more pharmaceutically acceptable excipients or carriers; wherein, the total content of the ion sodium in the effervescent solid pharmaceutical composition is equal to or lower than 1 mmol.

The second aspect of the invention relates to a process for the preparation of the effervescent solid pharmaceutical composition of the first aspect of the invention.

And, the third aspect of the invention relates to the effervescent solid pharmaceutical composition of the first aspect of the invention for use in therapy; and particularly in the treatment of chronic diseases.

DETAILED DESCRIPTION OF THE INVENTION

All terms as used herein in this application, unless otherwise stated, shall be understood in their ordinary meaning as known in the art. Other more specific definitions for certain terms as used in the present application are as set forth below and are intended to apply uniformly throughout the specification and claims unless an otherwise expressly set out definition provides a broader definition.

For the purposes of the present invention, any ranges given include both the lower and the upper endpoints of the range. Ranges and values given, such as temperatures, times, and the like, should be considered approximate, unless specifically stated.

The term "percentage (%) by weight" refers to the percentage of each ingredient of the composition in relation to the total weight.

The term "molar ratio" refers to the number of moles of a compound with respect to the number of moles of another compound. For example, it refers to the number of moles of one or more pharmaceutically acceptable acids or acid salts with respect to the number of moles of one or more alkaline earth metal carbonates or hydrogencarbonates.

The term "sodium" and "ion sodium" are synonyms and are used herein interchangeably.

The terms "essentially sodium free" or "essentially free of sodium" have the same meaning and are used interchangeable. They refer to pharmaceutical compositions comprising less than 1 mmol of sodium ion per unit dose.

The first aspect of the invention refers to an effervescent solid pharmaceutical composition. For the purposes of the invention, the term "solid composition" refers to any solid-state composition that is free of liquid media. Furthermore, the solid composition of the invention is a "pharmaceutical composition" comprising a "therapeutically effective amount of an active pharmaceutical ingredient" together with one or more "pharmaceutically acceptable excipients or carriers". The term "pharmaceutical composition" refers to a composition suitable for use in the pharmaceutical technology with medical use. The term "therapeutically effective amount of an active pharmaceutical ingredient" as used herein, refers to the amount of an active pharmaceutical ingredient that, when administered, is sufficient to prevent development of, or alleviate to some extent, one or more of the symptoms of the disease which is addressed. The dose of the active pharmaceutical ingredient administered according to this invention will of course be determined by the particular circumstances surrounding the case, including the compound administered, the route of administration, the particular condition being treated, and the similar considerations. For the purpose of the invention the terms "active pharmaceutical ingredient" and "API" have the same meaning and are used interchangeable. They refer to the active or central ingredient in the composition which causes the direct (therapeutically) effect on the diagnosis, prevention, treatment, cure or alleviation of a disease or condition.

For the purpose of the invention, the term "effervescent composition" refers to a composition that generally contains acid substances and carbonates or hydrogencarbonates that react rapidly in the presence of water to release carbon dioxide. Effervescent compositions are intended to be dissolved or dispersed in water before administration. Effervescent compositions of the invention fulfil the requirements established by the Ph. Eur. for the disintegration test of effervescent tablets which says as follows: "[ . . . ] place one tablet in a 250 ml beaker containing 200 ml of water R at 15-25° C. Numerous bubbles of gas are evolved. When the evolution of gas around the tablet or its fragments ceases, the tablet should have disintegrated, being either dissolved or dispersed in the water so that no agglomerates remain. Repeat the operation on five additional tablets. The tablets comply with the test if each of the six tablets used in the test disintegrates within 5 minutes [ . . . ]". Therefore, for the purpose of the invention, the term "effervescent time" refers to the time that elapses until the disintegration of the composition measured by the disintegration test of effervescent tablets of the European Pharmacopeia 9.8th edition, which comprises placing the composition in a beaker containing 200 mL of water R at 15-25° C.

For the purpose of the invention, the term "molar ratio" refers to the ratio between the acidic component and the alkaline component of the composition. Preferably, the term "molar ratio" refers to the ratio between the pharmaceutically acceptable acids or acid salts, or mixtures thereof; and the alkaline earth metal carbonates or hydrogencarbonates or mixtures thereof. For example, a "molar ratio" of X:Y, defines a composition of the invention that comprises X mol of the acidic component per Y mol of the alkaline component. Preferably, the "molar ratio" is expressed as X:1, defining a composition of the invention that comprises X mol of the acidic component per 1 mol of the alkaline component.

In an embodiment, the composition of the invention comprises a therapeutically effective amount of one or more water soluble active pharmaceutically ingredients. In an embodiment, the composition of the invention comprises a therapeutically effective amount of one or more active pharmaceutically ingredients selected from the group consisting of BCS class I, BCS class II, BCS class III and BCS class IV. In an other embodiment, the composition of the invention comprises a therapeutically effective amount of one or more active pharmaceutically ingredients selected from the group consisting of BCS class I, BCS class II and BCS class III.

The Biopharmaceutics Classification System (BCS) is a system to differentiate the drugs on the basis of their solubility and permeability. This system restricts the prediction using the parameters solubility and intestinal permeability. The solubility classification is based on a United States Pharmacopoeia (USP) aperture. The intestinal permeability classification is based on a comparison to the intravenous injection. According to the BCS drug substances are classified into four classes upon their solubility and permeability:

BCS Class I—high permeability, high solubility: Those compounds are well absorbed and their absorption rate is usually higher than excretion. Example: metoprolol, paracetamol.

BCS Class II—high permeability, low solubility: The bioavailability of those products is limited by their solvation rate. A correlation between the in vivo bioavailability and the in vitro solvation can be found. Example: glibenclamide, bicalutamide, ezetimibe, and aceclofenac.

BCS Class III—low permeability, high solubility: The absorption is limited by the permeation rate but the drug is solvated very fast. If the formulation does not change the permeability or gastro-intestinal duration time, then class I criteria can be applied. Example: cimetidine.

BCS Class IV—low permeability, low solubility: Those compounds have a poor bioavailability. Usually they are not well absorbed over the intestinal mucosa and a high variability is expected. Example: Bifonazole, hydrochlorothiazide and ritonavir.

In an embodiment, the composition of the invention comprises a therapeutically effective amount of one or more active pharmaceutical ingredients selected from the group of antiepileptics, as for example but not limited to: brivaracetam, carbamazepine, divalproex sodium, epidiolex, eslicarbazepine acetate, ethosuximide, ezogabine, felbamate, gabapentin, lacosamide, lamotrigine, levetiracetam, oxcarbazepine, perampanel, phenobarbital, phenytoin, pregabalin, primidone, rufinamide, tiagabine hydrochloride, topiramate, valproic acid, vigabatrin or zonisamide. In another embodiment, the composition of the invention comprises a therapeutically effective amount of one or more active pharmaceutical ingredients selected from the group of drugs for the treatment of anxiety disorders, as for example but not limited to: alprazolam, bromazepam, clobazam, clonazepam, diazepam, lorazepam or zolpidem. In another embodiment, the composition of the invention comprises a therapeutically effective amount of one or more active pharmaceutical ingredients selected from the group of antidepressives, as for example but not limited to: sertraline, trazodone, bupropion, vilazodone, amitriptyline, escitalopram, fluoxetine, duloxetine, venlafaxine or paroxetine.

In another embodiment, the composition of the invention comprises a therapeutically effective amount of one or more active pharmaceutical ingredients selected from the group of antithrombotics, as for example but not limited to: acenocumarol, acetylsalicylic acid, apixaban, betrixaban, clopidrogrel. dabigatran, edoxaban, enoxaparin, heparin, otamixaban, prasugrel, rivaroxaban, ticagrelor, ticlopidine or tirofiban. In another embodiment, the composition of the invention comprises a therapeutically effective amount of one or more active pharmaceutical ingredients selected from the group of antipsychotics, as for example but not limited to: amisulpride, aripiprazole, asenapine, blonanserin, brexipiprazole cariprazin, chlorpromazine, clozapine, haloperidol decanoate, iloperidone, lurasidone, mosapramine, olanzapine, paliperidone, quetiapine, risperidone, ziprasidone or zotepine. In another embodiment, the composition of the invention comprises a therapeutically effective amount of one or more active pharmaceutical ingredients selected from the group of anti-alzheimer, as for example but not limited to: donepezil, donepezil plus memantine, galantamine, memantine or rivastigmine. In another embodiment, the composition of the invention comprises a therapeutically effective amount of one or more active pharmaceutical ingredients selected from the group of antiparkinsonians, as for example but not limited to: bromocriptine, carbidopa plus levodopa, carbidopa plus entacapone plus levodopa, levodopa levodopa plus benserazide, pergolide, phenserine, pramipexole, rasagiline, ropinirole, rotigotine, safinamide or selegiline. In another embodiment, the composition of the invention comprises a therapeutically effective amount of one or more active pharmaceutical ingredients selected from the group of antihistaminics, as for example but not limited to: acrivastine, bilastine, cetirizine, ebastine, fexofenadine, levocetirizine, loratadine or rupatadine. In another embodiment, the composition of the invention comprises a therapeutically effective amount of one or more active pharmaceutical ingredients selected from the group of anti-vertigo medication, as for example but not limited to: betahistine, dimenhydrinate or meclizine. In another embodiment, the composition of the invention comprises a therapeutically effective amount of one or more active pharmaceutical ingredients selected from the group of antiosteoporotics, as for example but not limited to: alendronic acid, alendronate sodium, alendronate sodium plus vitamin 3, cholecalciferol, clodronic acid, etidronic acid, ibandronic acid, pamidronic acid, risedronic acid or zoledronic acid. In another embodiment, the composition of the invention comprises a therapeutically effective amount of one or more active pharmaceutical ingredients selected from the group of analgesics, as for example but not limited to: acetylsalicylic acid plus ascorbic acid, acetylsalicylic acid codeine, dexketoprofen, ibuprofen, ibuprofen plus pseudoephedrine, naproxen, nefopam, paracetamol or tramadol.

In another embodiment, the composition of the invention comprises a therapeutically effective amount of one or more active pharmaceutical ingredients selected from the group of drugs for neuropatic pain, as for example but not limited to: gabapentin and pregabalin. In another embodiment, the composition of the invention comprises a therapeutically effective amount of one or more active pharmaceutical ingredients selected from the group of drugs for the treatment of multiple sclerosis, as for example but not limited to: glatiramer acetate, teriflunomide, fingolimod, dimethyl fumarate or fampridine. In another embodiment, the composition of the invention comprises a therapeutically effective amount of one or more active pharmaceutical ingredients selected from the group of antidiabetics, as for example but not limited to: alogliptin, canaglifozin, dapaglifozin, empaglifozin, glibenclamide, glimepiride, glipizide, linagliptin, linagliptin plus metformin, pioglitazone, repaglinide, metformin, saxagliptin, sitagliptin, sitagliptin plus metformin, vildagliptin or vildagliptin plus metformin. In another embodiment, the composition of the invention comprises a therapeutically effective amount of one or more active pharmaceutical ingredients selected from the group of drugs for migraine, as for example but not limited to: almotriptan, rimegepant, rizatriptan, sumatriptan, ubrogepant or zolmitriptan. In another embodiment, the composition of the invention comprises a therapeutically effective amount of one or more active pharmaceutical ingredients selected from the group of drugs for attention deficit hyperactivity disorder, as for example but not limited to: atomoxetine, lisdexamfetamine or methylphenidate. In another embodiment, the composition of the invention comprises a therapeutically effective amount of one or more active pharmaceutical ingredients selected from the group of mucolytics, as for example but not limited to: acetylcysteine, ambroxol, bromhexine or carbocisteine. In another embodiment, the composition of the invention comprises a therapeutically effective amount of one or more active pharmaceutical ingredients selected from the group of drugs for asthma, as for example but not limited to: montelukast. In another embodiment, the composition of the invention comprises a therapeutically effective amount of one or more active pharmaceutical ingredients selected from the group of antiacids, as for example but not limited to: alginic acid plus calcium, alginic acid plus potassium, almagate, calcium plus magnesium, dimeticone, magaldrate or simethicone. In another embodiment, the composition of the invention comprises a therapeutically effective amount of one or more active pharmaceutical ingredients selected from the group of proton pump inhibitors, as for example but not limited to: dexlansoprazole, esomeprazole, lansoprazole, omeprazole magnesium, pantoprazole or rabeprazole. In another embodiment, the composition of the invention comprises a therapeutically effective amount of one or more active pharmaceutical ingredients selected from the group of h2 antagonists, as for example but not limited to: cimetidine, famotidine, nizatidine or ranitidine. In another embodiment, the composition of the invention comprises a therapeutically effective amount of one or more active pharmaceutical ingredients selected from the group of antihypertensives, as for example but not limited to: amlodipine, benazepril, bisoprolol, candesartan, diltiazem, enalapril plus lercanidipine, enalapril maletate, eplerenone, hydrochlorothiazide, irbesartan, lisinopril, lisinopril (Med), losartan, nebivolol plus hydrochlorothiazide, olmesartan, olmesartan plus amlodipine, olmesartan plus amlodipine plus hydrochlorothiazide, olmesartan plus hydrochlorothiazide, ramipril, spironolactone, telmisartan plus hydrochlorothiazide or triamterene plus hydrochlorothiazide In another embodiment, the composition of the invention comprises a therapeutically effective amount of one or more active pharmaceutical ingredients selected from the group of anti-cholesterol, as for example but not limited to: atorvastatin, ezetimibe, fenofibrate, fluvastatin, gemfibrozil, lipofen, pravastatin, rosuvastatin or simvastatin. In another embodiment, the composition of the invention comprises a therapeutically effective amount of one or more active pharmaceutical ingredients selected from the group of drugs for pulmonary arterial hypertension (pah), as for example but not limited to: bosentan, macitentan, sildenafil, tadalafil or telmisartan. In another embodiment, the composition of the invention comprises a therapeutically effective amount of one or more active pharmaceutical ingredients selected from the group of anti-infectives, as for example but not limited to: clarithromycin, itraconazole, levofloxacin, linezolid, nitrofurantoin, oseltamivir phosphate, rifaximin, valaciclovir or voriconazole. In another embodiment, the composition of the invention comprises a therapeutically effective amount of one or more active pharmaceutical ingredients selected from the group of urologicals, as for example but not limited to: dutasteride, dutasteride plus tamsulosin, mirabegron, oxybutynin, sildenafil (20 mg), solifenacin, tadalafil or tamsulosin. In another embodiment, the composition of the invention comprises a therapeutically effective amount of one or more active pharmaceutical ingredients selected from the group of immunosupressants, as for example but not limited to: pirfenidone. In another embodiment, the composition of the invention comprises a therapeutically effective amount of one or more active pharmaceutical ingredients selected from the group of antihypertension, as for example but not limited to: metoprolol or hydrochlorothiazide. In another embodiment, the composition of the invention comprises a therapeutically effective amount of one or more active pharmaceutical ingredients selected from the group of antiandrogen medication, as for example but not limited to: bicalutamide. In another embodiment, the composition of the invention comprises a therapeutically effective amount of one or more active pharmaceutical ingredients selected from the group of anti-hyperlipidemic, as for example but not limited to: ezetimibe. In another embodiment, the composition of the invention comprises a therapeutically effective amount of one or more active pharmaceutical ingredients selected from the group of antiinflammatory, as for example but not limited to: acetofenac. In another embodiment, the composition of the invention comprises a therapeutically effective amount of one or more active pharmaceutical ingredients selected from the group of antifungal, as for example but not limited to: bifonazole. In another embodiment, the composition of the invention comprises a therapeutically effective amount of one or more active pharmaceutical ingredients selected from the group of antiretroviral, as for example but not limited to: ritnonavir.

In a preferred embodiment, the composition of the invention comprises a therapeutically effective amount of an active pharmaceutical ingredient selected from the group consisting of levetiracetam, brivaracetam, lacosamide, paracetamol, diltiazem, memantine, quetiapine, donepezil, apixaban, bilastine, diazepam, escitalopram, rivastigmine, betahistine, sumatriptan, atomoxetine, ibuprofen, pregabalin, acetylcysteine, montelukast, rupatadine, simethicone, pantoprazole, ranitidine, metformin, atorvastatin, acetylsalicylic acid, alendronate sodium, sildenafil, metoprolol, glibenclamide, bicalutamide, ezetimibe, aceclofenac, cimetidine, bifonazole, hydrochlorothiazide, ritonavir and mixture thereof. In a preferred embodiment, the composition of the invention comprises a therapeutically effective amount of an active pharmaceutical ingredient selected from the group consisting of levetiracetam, brivaracetam, lacosamide, paracetamol, diltiazem, memantine, quetiapine, donepezil, apixaban, bilastine, diazepam, escitalopram, rivastigmine, betahistine, sumatriptan, atomoxetine, ibuprofen, pregabalin, acetylcysteine, montelukast, rupatadine, simethicone, pantoprazole, ranitidine, metformin, atorvastatin, acetylsalicylic acid, alendronate sodium, sildenafil and mixture thereof. In a preferred embodiment, the composition of the invention comprises a therapeutically effective amount of an active pharmaceutical ingredient selected from the group consisting of levetiracetam, brivaracetam, lacosamide, paracetamol, diltiazem, memantine and mixture thereof. In a preferred embodiment, the composition of the invention comprises a therapeutically effective amount of an active pharmaceutical ingredient selected from the group consisting of levetiracetam, brivaracetam, lacosamide and mixtures thereof.

In an embodiment, the composition of the invention comprises a therapeutically effective amount of levetiracetam. In an embodiment, the composition of the invention comprises a therapeutically effective amount of brivaracetam. In an embodiment, the composition of the invention comprises a therapeutically effective amount of lacosamide. In an embodiment, the composition of the invention comprises a therapeutically effective amount of paracetamol. In an embodiment, the composition of the invention comprises a therapeutically effective amount of diltiazem. In an embodiment, the composition of the invention comprises a therapeutically effective amount of memantine. In an embodiment, the composition of the invention comprises a therapeutically effective amount of quetiapine. In an embodiment, the composition of the invention comprises a therapeutically effective amount of donepezil, apixaban. In an embodiment, the composition of the invention comprises a therapeutically effective amount of Bilastine. In an embodiment, the composition of the invention comprises a therapeutically effective amount of diazepam. In an embodiment, the composition of the invention comprises a therapeutically effective amount of escitalopram. In an embodiment, the composition of the invention comprises a therapeutically effective amount of rivastigmine. In an embodiment, the composition of the invention comprises a therapeutically effective amount of betahistine. In an embodiment, the composition of the invention comprises a therapeutically effective amount of sumatriptan. In an embodiment, the composition of the invention comprises a therapeutically effective amount of atomoxetine. In an embodiment, the composition of the invention comprises a therapeutically effective amount of ibuprofen, In an embodiment, the composition of the invention comprises a therapeutically effective amount of pregabalin. In an embodiment, the composition of the invention comprises a therapeutically effective amount of acetylcysteine. In an embodiment, the composition of the invention comprises a therapeutically effective amount of montelukast. In an embodiment, the composition of the invention comprises a therapeutically effective amount of rupatadine. In an embodiment, the composition of the invention comprises a therapeutically effective amount of simethicone. In an embodiment, the composition of the invention comprises a therapeutically effective amount of pantoprazole. In an embodiment, the composition of the invention comprises a therapeutically effective amount of ranitidine. In an embodiment, the composition of the invention comprises a therapeutically effective amount of metformin. In an embodiment, the composition of the invention comprises a therapeutically effective amount of atorvastatin. In an embodiment, the composition of the invention comprises a therapeutically effective amount of acetylsalicylic acid. In an embodiment, the composition of the invention comprises a therapeutically effective amount of alendronate sodium. In an embodiment, the composition of the invention comprises a therapeutically effective amount of sildenafil.

In an embodiment, the composition of the invention comprises a therapeutically effective amount of metoprolol. In an embodiment, the composition of the invention comprises a therapeutically effective amount of glibenclamide. In an embodiment, the composition of the invention comprises a therapeutically effective amount of bicalutamide. In an embodiment, the composition of the invention comprises a therapeutically effective amount of ezetimibe. In an embodiment, the composition of the invention comprises a therapeutically effective amount of aceclofenac. In an embodiment, the composition of the invention comprises a therapeutically effective amount of cimetidine. In an embodiment, the composition of the invention comprises a therapeutically effective amount of bifonazole. In an embodiment, the composition of the invention comprises a therapeutically effective amount of hydrochlorothiazide. In an embodiment, the composition of the invention comprises a therapeutically effective amount of ritonavir. For the purpose of the present invention, all the aspects and embodiments (taken them alone or in combination with other embodiments disclosed above or below) disclosed in the invention with any one of the active ingredients taken separately forms also part of the invention.

In an embodiment, the composition of the invention comprises a therapeutically effective amount of the active pharmaceutical ingredient as defined above from 0.5% to 60% by weight of the composition, preferably from 0.5 to 50%, more preferably from 0.5 to 45%.

The composition of the present invention comprises a content of the ion sodium equal to or lower than 1 mmol. For the purpose of the invention, the measurement of the ion sodium in the compositions of the invention is performed by atomic absorption spectroscopy (AAS), atomic emission spectroscopy (AES), mass spectroscopy (MS), and/or any of such techniques with an inductively coupled plasma, such as ICP-AAS, ICP-AES and ICP-MS. However, other equivalent techniques may be used by the skilled person in the art.

In a preferred embodiment, the composition is free of ion sodium. The term "free of ion sodium" refers to a composition whose content of ion sodium is not detectable by any of the techniques defined above.

As it is mentioned above, the composition of the invention can be considered a "low alkaline earth metal content" compositions. For the purpose of the invention the term "low content of alkaline earth metal" refers to a composition whose content of alkaline earth metals is equal to or lower than 20% by weight of the weight of the composition. In an embodiment, the content of alkaline earth metal is equal to or lower than 15% by weight of the weight of the composition. In an embodiment, the content of alkaline earth metal is equal to or lower than 12% by weight of the weight of the composition. In an embodiment, the content of calcium is equal to or lower than 20% by weight of the weight of the composition. In an embodiment, the content of calcium is equal to or lower than 15% by weight of the weight of the composition. In an embodiment, the content of calcium is equal to or lower than 12% by weight of the weight of the composition. In an embodiment, the content of magnesium is equal to or lower than 10% by weight of the weight of the composition. In an embodiment, the content of magnesium is equal to or lower than 8% by weight of the weight of the composition. In an embodiment, the content of magnesium is equal to or lower than 5% by weight of the weight of the composition. For the purpose of the invention, the measurement of the alkaline earth metal ions, such as magnesium and calcium ions, in the compositions of the invention is performed by atomic absorption spectroscopy (AAS), atomic emission spectroscopy (AES), mass spectroscopy (MS), and/or any of such techniques with an inductively coupled plasma, such as ICP-AAS, ICP-AES and ICP-MS. However, other equivalent techniques may be used by the skilled person in the art. The content of calcium within a molecule of Calcium carbonate is 40.04% (w/w). The content of Magnesium within a molecule of Magnesium carbonate is 28.57% (w/w). In an embodiment, the content of alkaline earth metal in the composition of the invention is equal to or lower than 300 mg, preferably equal to or lower than 250 mg, preferably equal to or lower than 200 mg, even more preferably equal to or lower than 190 mg. In another embodiment, the content of Calcium in the composition of the invention is equal to or lower than 300 mg, preferably equal to or lower than 250 mg, preferably equal to or lower than 200 mg, even more preferably equal to or lower than 180 mg. In another embodiment, the content of Magnesium in the composition of the invention is equal to or lower than 200 mg, preferably equal to or lower than 180 mg, preferably equal to or lower than 150 mg, even more preferably equal to or lower than 50 mg.

Further, the composition of the invention fulfils the disintegration test of effervescent tablets established by the Ph. Eur., which consists in placing the composition of the invention in a 250 ml beaker containing 200 ml of water R at 15-25° C. and disintegrating within a time equal to or less than 5 minutes. In another embodiment, the composition of the invention disintegrates within a time equal to or less than 4 minutes, preferably equal to or less than 3 minutes; more preferably equal to or less than 2 minutes, much more preferably equal to or less than 1 minute and 30 seconds when placed in a 250 ml beaker containing 200 ml of water R at 15-25° C.

The term "pharmaceutically acceptable" refers to that product suitable for use in the pharmaceutical technology for preparing compositions with medical use. Each component must be acceptable in the sense of being compatible with the other ingredients of the composition. It must also be suitable for use in contact with the tissue or organ of humans and animals without excessive toxicity, irritation, allergic response, immunogenicity or other problems or complications commensurate with a reasonable benefit/risk ratio.

The composition of the invention comprises one or more pharmaceutically acceptable alkaline earth metal carbonates or hydrogencarbonates in an amount from 1 to 31% by weight of the composition, preferably from 1 to 28%, more preferably from 1 to 25%, much more preferably from 1 to 22%, even more preferably from 1 to 19%, even more preferably from 1 to 16%, even more preferably from 1 to 13%, and even more preferably from 1 to 12%. In another embodiment, the composition of the invention comprises one or more pharmaceutically acceptable alkaline earth metal carbonates or hydrogencarbonates in an amount from 2 to 31% by weight of the composition, preferably from 3 to 31%, more preferably from 4 to 31%, much more preferably from 5 to 31%, even more preferably from 6 to 31%, even more preferably from 7 to 31%. In another embodiment, the composition of the invention comprises one or more pharmaceutically acceptable alkaline earth metal carbonates or hydrogencarbonates in an amount from 2 to 28% by weight of the composition, preferably from 3 to 25%, more preferably from 5 to 22%, much more preferably from 5 to 19%, even more preferably from 5 to 16%, even more preferably from 5 to 13%, even more preferably from 7 to 12%. As it is mentioned above, these compositions are advantageous because of the low amount of alkaline earth metal carbonates, which results in a much less abrasive blend for compression. In another embodiment, the composition of the invention comprises one or more pharmaceutically acceptable alkaline earth metal carbonates or hydrogencarbonates in an amount from 26 to 31% by weight of the composition, preferably from 27.5 to 30%.

In an embodiment, the composition of the invention comprises one or more pharmaceutically acceptable alkaline earth metal carbonates or hydrogencarbonates selected from the group consisting of calcium carbonate, magnesium carbonate, calcium hydrogencarbonate, magnesium hydrogen carbonate and a mixture thereof. In an embodiment, the composition of the invention comprises calcium carbonate as a pharmaceutically acceptable alkaline earth metal carbonate. In an embodiment, the composition of the invention comprises a pharmaceutically acceptable alkaline earth metal carbonate; particularly calcium carbonate, in an amount from 1 to 31% by weight of the composition. All the embodiments as defined above for the pharmaceutically acceptable alkaline earth metal carbonates or hydrogencarbonates also apply for calcium carbonate.

The composition of the invention comprises one or more pharmaceutically acceptable acids, pharmaceutically acceptable acid salts or a mixture thereof, in an amount from 2 to 62% by weight of the composition, preferably from 2 to 56%, more preferably from 2 to 50%, much more preferably from 2 to 44%, even more preferably from 2 to 38%, even more preferably from 2 to 32%, even more preferably from 2 to 27%. In another embodiment, the composition of the invention comprises one or more pharmaceutically acceptable acids, pharmaceutically acceptable acid salts or a mixture thereof in an amount from 4 to 62% by weight of the composition, preferably from 6 to 62%, more preferably from 8 to 62%, much more preferably from 10 to 62%, even more preferably from 12 to 62%. In another embodiment, the composition of the invention comprises one or more pharmaceutically acceptable acids, pharmaceutically acceptable acid salts or a mixture thereof in an amount from 4 to 56% by weight of the composition, preferably from 6 to 50%, more preferably from 10 to 44%, much more preferably from 10 to 38%, even more preferably from 10 to 32%, even more preferably from 10% to 27%, even more preferably from 12 to 27%. In another embodiment, the composition of the invention comprises one or more pharmaceutically acceptable acids, pharmaceutically acceptable acid salts or a mixture thereof in an amount from 55 to 61% by weight of the composition, preferably from 55.5 to 60.5%. As it is mentioned above, these compositions are advantageous because of the low amount of pharmaceutically acceptable acids or pharmaceutically acceptable acid salts, which results in a much less abrasive blend for compression.

In an embodiment, the composition of the invention comprises one or more pharmaceutically acceptable acids.

In an embodiment, the composition of the invention comprises one or more pharmaceutically acceptable acids selected from the group consisting of an inorganic acid, a monocarboxylic acid, a dicarboxylic acid, a tricarboxylic acid and a keto- and an oxy-derivatives thereof. In an embodiment, the composition of the invention comprises one or more pharmaceutically acceptable acids selected from the group consisting of phosphoric acid, citric acid, glutamic acid, glutaric acid, malic acid, maleic acid, adipic acid, ascorbic acid, fumaric acid, tartaric acid, alpha- and beta-ketoglutaric acid, aspartic acid, mucic acid, gluconic acid, glucuronic acid, glycolic acid, lactic acid, lactobionic acid, malonic acid and succinic acid. In an embodiment, the composition of the invention comprises one or more pharmaceutically acceptable acids selected from the group consisting of citric acid, malic acid, maleic acid, glutamic acid, glutaric acid and alpha-ketoglutaric acid. Particularly in the amount and molar ratio as defined above and below in the present invention. In an embodiment, the composition of the invention comprises maleic acid as pharmaceutically acceptable acids. The presence of the hard acid, maleic acid, is specially preferred due to its good solubility in water and low hygroscopicity.

In an embodiment, the composition of the invention comprises one or more pharmaceutically acceptable acid salts. The term "acid salt" refers to a salt that produces an acidic solution after being dissolved in a solvent. The acidic solution formed by the acid salt is made during partial neutralization of diprotic or polyprotic acids. A half-neutralization occurs due to the remaining of replaceable hydrogen atoms from the partial dissociation of weak acids that have not been reacted with hydroxide ions (OH—) to create water molecules. For the purpose of the invention, an acid salt is an ionic compound consisted of an anion, contributed from a weak parent acid; and a cation, contributed from a strong parent base.

In an embodiment, the acid salt is an acid addition salt formed between an inorganic or organic acid and an amino acid. Examples of appropriate amino acids include, without limitation, glycine hydrochloride or alanine hydrochloride. In another embodiment, the acid salt is an acid addition salt selected from the group consisting of glycine hydrochloride, alanine hydrochloride, phenylalanine hydrochloride and leucine hydrochloride. Particularly in the amount and molar ratio as defined above and below in the present invention.

In an embodiment, the composition of the invention comprises a mixture of one or more pharmaceutically acceptable acids and one or more pharmaceutically acceptable acid salts. In an embodiment, the composition of the invention comprises a mixture of one or more pharmaceutically acceptable acid selected from the group consisting of phosphoric acid, citric acid, glutamic acid, glutaric acid, malic acid, maleic acid, adipic acid, ascorbic acid, fumaric acid, tartaric acid, $\alpha$- and $\beta$-ketoglutaric acid, aspartic acid, mucic acid, gluconic acid, glucuronic acid, glycolic acid, lactic acid, lactobionic acid, malonic acid, succinic acid; and one or more pharmaceutically acceptable acid salts selected from the group consisting of glycine hydrochloride, alanine hydrochloride, phenylalanine hydrochloride and leucine hydrochloride. In an embodiment, the composition of the invention comprises a mixture of one or more pharmaceutically acceptable acid selected from the group consisting of citric acid, malic acid and maleic acid; and one or more pharmaceutically acceptable acid salts selected from the group consisting of glycine hydrochloride, alanine hydrochloride, phenylalanine hydrochloride and leucine hydrochloride. Particularly in the amount and molar ratio as defined above and below in the present invention.

In an embodiment, the composition of the invention is one wherein when the composition is disintegrated after being placed in a beaker containing 200 mL of water R at 15-25° C., the resulting water solution has a pH from 1.5 to 7; particularly a pH from 2 to 6.5; and more particularly from 2.5 to 6.5. The above-mentioned pH allows a quicker disintegration allowing the improvement of the bioavailability of the active pharmaceutical ingredient and also having a pleasant taste and thus, improving the adherence to the treatment. The above-mentioned pH from 2.5 to 6.5 allows a quicker disintegration and dissolution resulting in a transparent solution allowing and enhanced improvement of the bioavailability of the active pharmaceutical ingredient and also having a pleasant taste and thus, improving the compliance of the treatment. Furthermore, the above-mentioned pH of the water solution obtained after the disintegration of the composition of the present invention also enhances its tolerability and also the tolerability of other drugs that cause a reduction of the gastric pH after its administration. In a preferred embodiment, compositions of the invention comprise pharmaceutically acceptable acids or acid salts, or a mixture thereof; and alkaline earth metal carbonates or hydrogencarbonates or a mixture thereof in a molar ratio from 0.5:1 to 8:1; preferably from 0.5:1 to 5:1, more preferably from 0.8:1 to 3:1. In an embodiment, the molar ratio between the pharmaceutically acceptable acids, acid salts, or a mixture thereof, and the alkaline earth metal carbonates or hydrogen carbonates or mixtures thereof is from 1.5:1 to 2.5:1. In a more preferred embodiment, compositions of the invention comprise pharmaceutically acceptable acids or acid salts, or a mixture thereof; and calcium carbonate in a molar ratio from 0.5:1 to 8:1; preferably from 0.5:1 to 5:1, more preferably from 0.8:1 to 3:1. In an embodiment, the molar ratio between the pharmaceutically acceptable acids, pharmaceutically acceptable acid salts, or mixture thereof, and the calcium carbonate is from 1:1 to 2.5:1.

In an embodiment, the composition of the invention comprises one or more pharmaceutically acceptable alkaline earth metal carbonates or hydrogencarbonates in an amount from 7 to 12% by weight of the composition, and, one or more pharmaceutically acceptable acids or acid salts or a mixture thereof in an amount from 12 to 27% by weight of the composition. In an embodiment, the composition of the invention comprises one or more pharmaceutically acceptable alkaline earth metal carbonates or hydrogencarbonates in an amount from 7 to 12% by weight of the composition; and one or more pharmaceutically acceptable acids or acid salts in an amount from 12 to 27% by weight of the composition; wherein the molar ratio between the one or more pharmaceutically acceptable acids or acid salts; and the one or more alkaline earth metal carbonates or hydrogencarbonates is from 0.5:1 to 8:1; preferably from 0.5:1 to 5:1, more preferably from 0.8:1 to 3:1. In an embodiment, the molar ratio between the one or more pharmaceutically acceptable acids or acid salts, and the one or more alkaline earth metal carbonates or hydrogencarbonates is from 1.5:1 to 2.5:1.

In an embodiment, the composition of the invention comprises calcium carbonate in an amount from 7 to 12% by weight of the composition, and, one or more pharmaceutically acceptable acids or acid salts in an amount from 12 to 27% by weight of the composition. In an embodiment, the composition of the invention comprises calcium carbonate in an amount from 7 to 12% by weight of the composition; and one or more pharmaceutically acceptable acids or acid salts in an amount from 12 to 27% by weight of the composition; wherein the molar ratio between the one or more pharmaceutically acceptable acids or acid salts; and the calcium carbonate is from 0.5:1 to 8:1; preferably from 0.5:1 to 5:1, more preferably from 0.8:1 to 3:1. In an embodiment, the molar ratio between the one or more pharmaceutically acceptable acids or acid salts, and the calcium carbonate is from 1.5:1 to 2.5:1. In an embodiment, the composition of the invention comprises calcium carbonate in an amount from 27.5 to 30% by weight of the composition, and, one or more pharmaceutically acceptable acids or acid salts in an amount from 55.5 to 60.5% by weight of the composition. In an embodiment, the composition of the invention comprises calcium carbonate in an amount from 27.5 to 30% by weight of the composition; and one or more pharmaceutically acceptable acids or acid salts in an amount from 55.5 to 60.5% by weight of the composition; wherein the molar ratio between the one or more pharmaceutically acceptable acids or acid salts; and the calcium carbonate is from 0.5:1 to 8:1; preferably from 0.5:1 to 5:1, more preferably from 0.8:1 to 3:1. In an embodiment, the molar ratio between the one or more pharmaceutically acceptable acids or acid salts, and the calcium carbonate is from 1:1 to 2.5:1.

The amount of the "effervescent acid-base couple" of the composition of the present invention is from 3 to 93% by weight of the composition, particularly from 3 to 80%; particularly from 6% to 80%; more particularly from 9% to 75%, much more particularly from 12 to 66%, even more particularly from 15 to 57%. In an embodiment, the amount of the "effervescent acid-base couple" of the composition of the present invention is from 18 to 52% by weight of the composition, particularly from 18 to 57%, more particularly from 20 to 48%, much more particularly from 20 to 42%. In another embodiment, the amount of the "effervescent acid-base couple" of the composition of the present invention is from 26 to 36% by weight of the composition. The terms "effervescent acid-base couple", "effervescent acid-base pair", "effervescent couple" and "effervescent pair" have the same meaning and are used interchangeable. They refer to the sum of the amount of the acidic component and an alkaline/basic component. For the purpose of the present invention the term "acidic component" refers to the sum of the weights of the pharmaceutically acceptable acid and/or acid salts and the term "basic component" refers to the amount of the one or more pharmaceutically acceptable alkaline earth metal carbonate or hydrogencarbonates present in the composition. As it is mentioned above, the amount of the effervescent pair of the present invention is lower than 93% by weight of the composition, particularly lower than 80%, preferably lower than 75%, more preferably lower than 66%, much more preferably lower than 57%, even more preferably lower than 48%. In an embodiment the amount of the effervescent pair of the composition is lower than 42% by weight of the composition. In another embodiment the amount of the effervescent pair of the composition is lower than 91% by weight of the composition, particularly equal to or lower than 90.5%. Compositions of the invention are advantageous because contents of the effervescent pair lower than those disclosed in the state of the art are much less abrasive and thereby, they prolong useful life of the tabletting tools, particularly when dry granulation methods or direct compression are used.

In an embodiment, the composition of the invention is one which comprises:

citric acid as the pharmaceutically acceptable acid;
  one or more alkaline earth metal carbonate; particularly calcium carbonate; and
  the molar ratio between the citric acid and the alkaline earth metal carbonate is from 0.5:1 to 5:1; particularly from 0.8:1 to 2:1.

In an embodiment, the composition of the invention is one which comprises:

maleic acid as the pharmaceutically acceptable acid;
  one or more alkaline earth metal carbonates; particularly calcium carbonate; and
  the molar ratio between the pharmaceutically acceptable acid and the alkaline earth metal carbonate is from 0.8:1 to 5:1; preferably from 1.5:1 to 3:1.

In an embodiment, the composition of the invention comprises a therapeutically effective amount of an active pharmaceutical ingredient, particularly those mentioned above, having a particle size distribution such that $D(v, 50)$ is greater than 67 μm, particularly greater than 80 μm, more particularly greater than 100 μm, and much more particularly greater than 125 μm. In a preferred embodiment, the active pharmaceutical ingredients is levetiracetam and have a particle size distribution such that $D(v, 50)$ is greater than 67 μm, particularly greater than 80 μm, more particularly greater than 100 μm, much more particularly greater than 125 μm. The term "$D(v, 50)$", also known as volume median diameter, refers to the diameter where 50% of the volume distribution is above and 50% is below. The $D(v, 50)$ can be measured by the known methods disclosed in the state of the art. Commonly, the $D(v,50)$ is calculated by measuring the characteristic equivalent sphere diameter, known as volume diameter, by laser diffraction. In the present invention the $D(v,50)$ has been determined using a Malvern apparatus. However, other equivalent apparatus may be used by the skilled person in the art. Compositions of the invention comprising an active pharmaceutical ingredient of those mentioned above, particularly levetiracetam, having $D(v, 50)$ of the embodiment are advantageous for the preparation of effervescent compositions by direct compression, dry granulation and moisture activated dry granulation (MADG).

In an embodiment, the composition of the invention comprises a therapeutically effective amount of an active pharmaceutical ingredient, particularly those mentioned above, having a particle size distribution such that $D(v, 10)$ is greater than 12 μm, particularly greater than 25 μm, more particularly greater than 30 μm, and much more particularly greater than 35 μm. In a preferred embodiment, the active pharmaceutical ingredients is levetiracetam and have a particle size distribution such that $D(v, 10)$ is greater than 12 μm, particularly greater than 25 μm, more particularly greater than 30 μm, and much more particularly greater than 35 μm. The term "$D(v, 10)$" refers to the diameter where 10% of the volume distribution is below this value. The $D(v, 10)$ can be measured by the known methods disclosed in the state of the art. Commonly, the $D(v, 10)$ is calculated by measuring the characteristic equivalent sphere diameter, known as volume diameter, by laser diffraction. In the present invention the $D(v,10)$ has been determined by using a Malvern apparatus. However, other equivalent apparatus may be used by the skilled person in the art. Compositions of the invention comprising an active pharmaceutical ingredient of those mentioned above, particularly levetiracetam, having $D(v, 10)$ of the embodiment are advantageous for the preparation of effervescent compositions by direct compression, dry granulation and moisture activated dry granulation (MADG).

In an embodiment, the composition of the invention comprises a therapeutically effective amount of an active pharmaceutical ingredient, particularly those mentioned above, having a particle size distribution such that $D(v, 90)$ is greater than 213 μm; particularly greater than 265 μm, more particularly greater than 330 μm, and much more particularly greater than 410 μm. In a preferred embodiment, the active pharmaceutical ingredient is levetiracetam and have a particle size distribution such that $D(v, 90)$ is greater than 213 μm; particularly greater than 265 μm, more particularly greater than 330 μm, and much more particularly greater than 410 μm. The term "$D(v, 90)$" refers to the diameter where 90% of the volume distribution is below this value. The $D(v, 90)$ can be measured by the known methods disclosed in the state of the art. Commonly, the $D(v, 90)$ is calculated by measuring the characteristic equivalent sphere diameter, known as volume diameter, by laser diffraction. In the present invention the $D(v,90)$ has been determined by using a Malvern apparatus. However, other equivalent apparatus may be used by the skilled person in the art. Compositions of the invention comprising an active pharmaceutical ingredient of those mentioned above, particularly levetiracetam, having $D(v, 90)$ of the embodiment are advantageous for the preparation of effervescent compositions by direct compression, dry granulation and moisture activated dry granulation (MADG).

In an embodiment, the composition of the invention comprises a therapeutically effective amount of an active pharmaceutical ingredient, particularly those mentioned above, having a particle size span equal to or lower than 3.5, particularly equal to or lower than 3, more particularly equal to or lower than 2.5, and much more particularly equal to or lower than 2. In a preferred embodiment, the active pharmaceutical ingredient is levetiracetam and have a particle size span from 2 to 3; particularly from 2.2 to 2.8, more particularly from 2.3 to 2.5. The terms "particle size span" or "PS span" have the same meaning and are used interchangeable. They refer to the width of the peak indicating the monomodal particle size distribution. The particle size span is calculated by the following formula $[d(v,90)-d(v,10)]/d(v,50)$. For the purpose of the present invention, the $D(v, 90)$, $D(v, 10)$ and $D(v, 50)$ can be measured by the known methods disclosed in the state of the art as defined above. Compositions of the invention comprising an active pharmaceutical ingredient of those mentioned above, particularly levetiracetam, having a particle size span of the embodiment are advantageous for the preparation of effervescent compositions by direct compression, dry granulation and moisture activated dry granulation (MADG).

In an embodiment, the composition of the invention comprise a therapeutically effective amount of an active pharmaceutical ingredient, particularly those mentioned above, more particularly levetiracetam, having a particle size distribution such that: $D(v, 50)$ is greater than 67 $\mu m$; $D(v, 10)$ is greater than 12 $\mu m$; and $D(v, 90)$ is greater than 213 $\mu m$. In a particular embodiment, the composition of the invention comprise a the therapeutically effective amount of an active pharmaceutical ingredient, particularly those mentioned above, more particularly levetiracetam, having a particle size distribution such that: $D(v, 50)$ is greater than 80 $\mu m$; $D(v, 10)$ is greater than 25 $\mu m$; and $D(v, 90)$ is greater than 265 $\mu m$. In a more particular embodiment, the composition of the invention comprise a therapeutically effective amount of an active pharmaceutical ingredient, particularly those mentioned above, more particularly levetiracetam, having a particle size distribution such that: $D(v, 50)$ is greater than 100 $\mu m$; $D(v, 10)$ is greater than 30 $\mu m$; and $D(v, 90)$ is greater than 330 $\mu m$. In a much more particular embodiment, the composition of the invention comprise a therapeutically effective amount of an active pharmaceutical ingredient, particularly those mentioned above, more particularly levetiracetam, having a particle size distribution such that: $D(v, 50)$ is greater than 125 $\mu m$; $D(v, 10)$ is greater than 35 $\mu m$; and $D(v, 90)$ is greater than 410 $\mu m$. Compositions of the invention comprising an active pharmaceutical ingredient of those mentioned above, particularly levetiracetam, having a particle size distribution $D(v,10)$, $D(v,50)$ and $D(v,90)$ of the embodiment are advantageous for the preparation of effervescent compositions by direct compression, dry granulation and moisture activated dry granulation (MADG).

In an embodiment, the composition of the invention is a granulated composition that comprises a therapeutically effective amount of an active pharmaceutical ingredient. As it is mentioned above, these granulated compositions of the present invention can be prepared by any method known in the state of the art as for example, but not limited to, dry granulation, wet granulation, Moisture Activated Dry Granulation (MADG) and direct compression. In an embodiment, the composition of the invention is a wet granulated composition and the therapeutically effective amount of an active pharmaceutical ingredient; particularly having a particle size distribution $D(v, 50)$, $D(v, 10)$, $D(v, 90)$, particle size span, and a combination of $D(v, 50)$, $D(v, 10)$ and $D(v, 90)$ as defined above for the direct compression, dry granulation and/or MADG compositions of the present invention. In a preferred embodiment, the active pharmaceutical ingredient is levetiracetam.

The compositions of the present invention comprise one or more pharmaceutically acceptable excipients or carriers. The term "pharmaceutically acceptable excipients or carriers" refers to that excipients or carriers suitable for use in the pharmaceutical technology for preparing compositions with medical use. The appropriate excipients and/or carriers, and their amounts, can readily be determined by those skilled in the art according to the type of formulation being prepared.

The solid compositions of the invention can be formulated in any form that includes any single unit dosage form and any multiple unit dosage forms. The term "single unit" encompasses one entity such as a single tablet, a single capsule. The term "single unit dosage form" defines a dosage form which consists only of one unit which contains the therapeutically effective amount of the active ingredient. The term "multiple unit dosage form" defines a dosage from which consists of more than one unit which contains the therapeutically effective amount of the active ingredient. Usually the multiple unit dosage forms are based on subunits such as granules, pellets or minitablets. They are usually delivered in hard gelatine capsules or transformed into tablets. Thus, it is also part of the invention a unit dosage form which comprises the composition of the present invention. In an embodiment, the unit dosage form which comprises the composition of the present invention is a single unit dosage form. In an embodiment, the unit dosage from which comprises the composition of the present invention is a multiple unit dosage form.

In an embodiment, the compositions of the present invention comprise one or more pharmaceutically acceptable excipients and/or carriers selected from the group consisting of diluent, lubricant, binder, glidant, disintegrant, lubricant and mixtures thereof.

The terms "filler" and "diluent" have the same meaning and are used interchangeably. They refer to any pharmaceutically acceptable excipient or carrier (material) that fill out the size of a composition, making it practical to produce and convenient for the consumer to use. Materials commonly used as filler include calcium carbonate, magnesium carbonate, calcium lactate, calcium phosphate, dibasic calcium phosphate, tribasic calcium sulfate, calcium carboxymethyl cellulose, cellulose, cellulose products such as microcrystalline cellulose and its salts, dextrin and dextrin derivatives, dextrose, fructose, lactitol, lactose, starches or modified starches, magnesium carbonate, magnesium oxide, maltitol, maltodextrins, maltose, mannitol, sorbitol, starch and starch derivatives, polydextrose, polyethylene glycol, sucrose, sugar, xylitol, inositol, isomalt, (cross)polyvinylpyrrolidone, erythritol, sucrose, sugar, trehalose and mixtures thereof. In an embodiment, the composition of the invention is one wherein the pharmaceutically acceptable excipients or carriers comprises one or more filler selected from the group consisting of xylitol, mannitol, sorbitol, inositol, isomalt, maltitol, lactitol, adventose, Tabletose®, Ludipress®, Perlitol®, lactose fast flo, xilitab, Xylisorb®, lactose and povidone; particularly mannitol, Isomalt, adventose, Tabletose®, Ludipress®, Perlitol®, lactose fast flo, xilitab and Xylisorb®; more particularly isomalt. In an embodiment, the composition of the invention is one wherein the pharmaceutically acceptable excipients or carriers comprise one or more filler, preferably isomalt, in an amount from 10 to 50% by weight of the composition. The presence of the non-reducing sugar, isomalt, is specially preferred due to its high solubility in water, low hygroscopicity, good compressibility and glidant properties, as well as its good palatability.

The term "lubricant" refers to a substance that prevents composition ingredients from clumping together and from sticking to the tablet punches or capsule filling machine and improves flowability of the composition mixture. Materials commonly used as a lubricant include sodium oleate, sodium stearate, sodium benzoate, sodium stearate, sodium chloride, stearic acid, sodium stearyl fumarate, calcium stearate, magnesium stearate, magnesium lauryl sulphate, sodium lauryl sulphate, sodium stearyl fumarate, sucrose esters or fatty acid, zinc, zinc stearate, stearic acid, sucrose stearate, talc, leucine, polyethylene glycol, glyceryl behenate, glyceryl monostearate, myristic acid, palmitic acid, poloxamer, potassium benzoate and mixtures thereof; particularly polyethylene glycol (PEG6000 and PEG4000), magnesium stearate, leucine, sodium benzoate and sodium lauryl sulphate; more particularly leucine, polyethylene glycol (PEG6000 and PEG4000) and magnesium stearate. The presence of a lubricant is particularly preferred when the composition is a tablet to improve the tableting process. In an embodiment, the composition of the invention is one wherein the pharmaceutically acceptable excipients or carriers comprise one or more lubricants, preferably leucine, in an amount from 0.1 to 50% by weight of the composition, preferably form 0.5 to 25% by weight of the composition, even more preferably from 1 to 15% by weight of the composition. In an embodiment, the composition of the invention is one wherein the pharmaceutically acceptable excipients or carriers comprise one or more lubricants, being the lubricant leucine. The presence of leucine is specially preferred due to its high solubility in water, good palatability, and also its good lubricant and anti-adherent properties.

The term "binder" refers to any pharmaceutically acceptable compound having binding properties. Materials commonly used as binders include povidone such as polyvinylpyrrolidone K30, methylcellulose polymers, hydroxyethyl cellulose, hydroxyethylmethyl cellulose, hydroxypropyl cellulose, L-hydroxypropyl cellulose (low substituted), hydroxypropyl methyl cellulose (HPMC), sodium carboxymethyl cellulose, carboxymethylene, carboxymethyl hydroxyethyl cellulose and other cellulose derivatives, starches or modified starches, acacia, agar, alginic acid, ammonium alginate, chitosan, dextrates, dextrin, dextrose, guar gum, lactose, fructose, lactitol, lactose, maltose, maltitol, maltodextrin, maltose, polydextrose, polyethylene oxide, povidone, sodium alginate, sucrose, sugar, sorbitol, xylitol and a mixture thereof. In an embodiment, the composition of the invention is one wherein the pharmaceutically acceptable excipients or carriers comprise one or more binder. In an embodiment, the composition of the invention is one wherein the pharmaceutically acceptable excipients or carriers comprise one or more binders in an amount from 0% to 10% by weight of the composition.

In an embodiment, the composition of the invention is a direct compression composition and the one or more binders is selected from the group consisting of starches or modified starches, fructose, lactitol, lactose, maltose, maltodextrin, mannitol, sorbitol, sugar, xylitol, dextrin, polyvinylpyrrolidone, lactose and mixture thereof.

The term "glidant" refers to a substance which improves the flow characteristics of powder mixtures in the dry state. Materials commonly used as a glidant include magnesium stearate, colloidal silicon dioxide, cellulose, hydrophobic colloidal silica, magnesium oxide, magnesium silicate, magnesium trisilicate, sodium stearate, starch, talc or a mixture thereof. In an embodiment, the composition of the invention is one wherein the pharmaceutically acceptable excipients or carriers comprises one or more glidant. In an embodiment, the composition of the invention is one wherein the pharmaceutically acceptable excipients or carriers comprise one or more glidant in an amount from 0% to 10% by weight of the composition.

The term "disintegrant" refers to a substance which helps the composition break apart and release the active ingredient from it, particularly tablet and capsules. Materials commonly used as a disintegrant include agar, alginic acid, asparagine, calcium alginate, chitosan, colloidal silicon dioxide, corn starch and corn starch derivatives, croscarmellose sodium, crospovidone, glycine, guar gum, hydroxypropyl cellulose, hydroxypropyl starch, lactose, maltose, methyl cellulose, povidone, sodium alginate, sodium starch glycolate, starch and starch derivatives or a mixture thereof. In an embodiment, the composition of the invention is one wherein the pharmaceutically acceptable excipients or carriers comprises one or more disintegrants. In an embodiment, the composition of the invention is one wherein the pharmaceutically acceptable excipients or carriers comprise one or more disintegrant in an amount from 0% to 10% by weight of the composition. In the case of effervescent compositions, these may not contain disintegrants because the effervescent pair may act as such.

Additionally, the compositions of the present invention may contain other ingredients, such as flavours, taste masking agents, sweeteners, colorants and other components known in the state of the art for use in oral solid formulations.

The term "sweetener" refers to a substance which gives the basic taste of sweetness to the composition. Materials commonly used as a sweeteners include acesulfame potassium, aspartame, cyclamic acid and cyclamic salts, saccharin and saccharin salts, tagatose, thaumatin, sucralose, or a mixture thereof.

In an embodiment, the composition of the present invention comprises:
  a therapeutically effective amount of an active pharmaceutical ingredient,
  one or more pharmaceutically acceptable alkaline earth metal carbonates in an amount from 1 to 35% by weight of the composition; particularly calcium carbonate,
  one or more pharmaceutically acceptable acids in an amount from 2 to 65% by weight of the composition; particularly citric acid, maleic acid or mixture thereof,
  one or more lubricants in an amount from 1 to 10% by weight; particularly leucine, and
  optionally one or more additional pharmaceutically acceptable excipients or carriers,
  being the sum of ingredients 100%.
In an embodiment, the composition of the present invention comprises:
  a therapeutically effective amount of an active pharmaceutical ingredient,
  from 1 to 35% by weight of the composition of calcium carbonate, magnesium carbonate or mixture thereof as pharmaceutically acceptable alkaline earth metal carbonates;
  from 2 to 65% by weight of the composition of citric acid, maleic acid or mixture thereof as pharmaceutically acceptable acids,
  from 1 to 10% by weight of leucine as lubricant and
  optionally one or more additional pharmaceutically acceptable excipients or carriers,
  being the sum of ingredients 100%.
In an embodiment, the composition of the present invention comprises:
  a therapeutically effective amount of an active pharmaceutical ingredient,
  from 1 to 35% by weight of the composition of calcium carbonate as pharmaceutically acceptable alkaline earth metal carbonates;
  from 2 to 65% by weight of the composition of maleic acid as pharmaceutically acceptable acids,
  from 1 to 10% by weight of leucine as lubricant and
  optionally one or more additional pharmaceutically acceptable excipients or carriers,
  being the sum of ingredients 100%.
In an embodiment, the composition of the present invention comprises:
  a therapeutically effective amount of an active pharmaceutical ingredient,
  one or more pharmaceutically acceptable alkaline earth metal carbonates in an amount from 1 to 22% by weight of the composition; particularly calcium carbonate, one or more pharmaceutically acceptable acids in an amount from 2 to 44% by weight of the composition; particularly citric acid, maleic acid or mixture thereof, one or more diluents in an amount from 5 to 50% by weight; particularly isomalt, one or more lubricants in an amount from 1 to 10% by weight; particularly leucine, and optionally one or more additional pharmaceutically acceptable excipients or carriers, being the sum of ingredients 100%.

In an embodiment, the composition of the present invention comprises:

a therapeutically effective amount of an active pharmaceutical ingredient, from 1 to 22% by weight of the composition of calcium carbonate, magnesium carbonate or mixture thereof as pharmaceutically acceptable alkaline earth metal carbonates;

from 2 to 44% by weight of the composition of citric acid, maleic acid or mixture thereof as pharmaceutically acceptable acids, from 5 to 50% by weight of isomalt as diluents, from 1 to 10% by weight of leucine as lubricant and optionally one or more additional pharmaceutically acceptable excipients or carriers, being the sum of ingredients 100%.

In an embodiment, the composition of the present invention comprises:

a therapeutically effective amount of an active pharmaceutical ingredient, from 1 to 22% by weight of the composition of calcium carbonate as pharmaceutically acceptable alkaline earth metal carbonates;

from 2 to 44% by weight of the composition of maleic acid as pharmaceutically acceptable acids, from 5 to 50% by weight of isomalt as diluents, from 1 to 10% by weight of leucine as lubricant and optionally one or more additional pharmaceutically acceptable excipients or carriers, being the sum of ingredients 100%.

In an embodiment, the composition of the present invention comprises:

a therapeutically effective amount of an active pharmaceutical ingredient; particularly levetiracetam, one or more pharmaceutically acceptable alkaline earth metal carbonates in an amount from 1 to 22% by weight of the composition; particularly calcium carbonate, one or more pharmaceutically acceptable acids in an amount from 2 to 44% by weight of the composition; particularly citric acid, maleic acid or mixture thereof, one or more diluents in an amount from 5 to 50% by weight; particularly isomalt, one or more lubricants in an amount from 1 to 10% by weight; particularly leucine, and optionally one or more additional pharmaceutically acceptable excipients or carriers, being the sum of ingredients 100%.

In an embodiment, the composition of the present invention comprises:

a therapeutically effective amount of an active pharmaceutical ingredient; particularly levetiracetam, one or more pharmaceutically acceptable alkaline earth metal carbonates in an amount from 1 to 16% by weight of the composition; particularly calcium carbonate, one or more pharmaceutically acceptable acids in an amount from 2 to 32% by weight of the composition; particularly citric acid, maleic acid or mixture thereof, one or more diluents in an amount from 5 to 45% by weight; particularly isomalt, and one or more lubricants in an amount from 1 to 8% by weight; particularly leucine, and optionally one or more additional pharmaceutically acceptable excipients or carriers, being the sum of ingredients 100%.

In an embodiment, the composition of the present invention comprises:

a therapeutically effective amount of an active pharmaceutical ingredient in an amount from 5 to 45% by weight of the composition; particularly levetiracetam, one or more pharmaceutically acceptable alkaline earth metal carbonates in an amount from 1 to 15% by weight of the composition; particularly calcium carbonate, one or more pharmaceutically acceptable acids in an amount from 2 to 30% by weight of the composition; particularly citric acid, maleic acid or mixture thereof, one or more diluents in an amount from 5 to 45% by weight; particularly isomalt, one or more lubricants in an amount from 1 to 8% by weight; particularly leucine, and optionally one or more additional pharmaceutically acceptable excipients or carriers, being the sum of ingredients 100%.

In an embodiment, the composition of the present invention comprises:

a therapeutically effective amount of an active pharmaceutical ingredient in an amount from 20 to 45% by weight of the composition; particularly levetiracetam, one or more pharmaceutically acceptable alkaline earth metal carbonates in an amount from 5 to 15% by weight of the composition; particularly calcium carbonate, one or more pharmaceutically acceptable acids in an amount from 10 to 30% by weight of the composition; particularly citric acid, maleic acid or mixture thereof, one or more diluents in an amount from 9 to 45% by weight; particularly isomalt, one or more lubricants in an amount from 1 to 8% by weight; particularly leucine, and optionally one or more additional pharmaceutically acceptable excipients or carriers, being the sum of ingredients 100%.

In an embodiment, the composition of the present invention comprises:

a therapeutically effective amount of an active pharmaceutical ingredient; particularly lacosamide, one or more pharmaceutically acceptable alkaline earth metal carbonates in an amount from 1 to 35% by weight of the composition; particularly calcium carbonate, one or more pharmaceutically acceptable acids in an amount from 2 to 65% by weight of the composition; particularly citric acid, maleic acid or mixture thereof, one or more lubricants in an amount from 1 to 10% by weight; particularly polyethylene glycol (PEG6000 and PEG4000), magnesium stearate, leucine, sodium benzoate, sodium lauryl sulphate, or mixture thereof and optionally one or more additional pharmaceutically acceptable excipients or carriers, being the sum of ingredients 100%.

In an embodiment, the composition of the present invention comprises:

a therapeutically effective amount of an active pharmaceutical ingredient; particularly lacosamide, one or more pharmaceutically acceptable alkaline earth metal carbonates in an amount from 5 to 35% by weight of the composition; particularly calcium carbonate, one or more pharmaceutically acceptable acids in an amount from 10 to 65% by weight of the composition; particularly citric acid, maleic acid or mixture thereof, one or more lubricants in an amount from 1 to 10% by weight; particularly leucine, sodium benzoate, polyethylene glycol 6000 or mixture thereof and optionally one or more additional pharmaceutically acceptable excipients or carriers, being the sum of ingredients 100%.

In an embodiment, the composition of the present invention comprises:

a therapeutically effective amount of an active pharmaceutical ingredient; particularly lacosamide, one or more pharmaceutically acceptable alkaline earth metal carbonates in an amount from 10 to 35% by weight of the composition; particularly calcium carbonate, one or more pharmaceutically acceptable acids in an amount from 30 to 65% by weight of the composition; particularly citric acid, maleic acid or mixture thereof, one or more lubricants in an amount from 1 to 10% by weight; particularly leucine, sodium benzoate, polyethylene glycol 6000 or mixture thereof and optionally one or more additional pharmaceutically acceptable excipients or carriers, being the sum of ingredients 100%.

In an embodiment, the composition of the present invention comprises:

a therapeutically effective amount of an active pharmaceutical ingredient; selected from the group consisting of levetiracetam, brivaracetam, lacosamide, paracetamol, diltiazem, memantine, quetiapine, donepezil, apixaban, bilastine, diazepam, escitalopram, rivastigmine, betahistine, sumatriptan, atomoxetine, ibuprofen, pregabalin, acetylcysteine, montelukast, rupatadine, simethicone, pantoprazole, ranitidine, metformin, atorvastatin, acetylsalicylic acid, alendronate sodium, sildenafil and mixture thereof.

one or more pharmaceutically acceptable alkaline earth metal carbonates in an amount from 1 to 35% by weight of the composition; particularly calcium carbonate, one or more pharmaceutically acceptable acids in an amount from 2 to 65% by weight of the composition; particularly citric acid, maleic acid or mixture thereof, one or more lubricants in an amount from 1 to 10% by weight; particularly polyethylene glycol (PEG6000 and PEG4000), magnesium stearate, leucine, sodium benzoate, sodium lauryl sulphate, or mixture thereof and optionally one or more additional pharmaceutically acceptable excipients or carriers, being the sum of ingredients 100%.

In an embodiment, the composition of the present invention comprises:

a therapeutically effective amount of an active pharmaceutical ingredient; selected from the group consisting of levetiracetam, brivaracetam, lacosamide, paracetamol, diltiazem, memantine, quetiapine, donepezil, apixaban, bilastine, diazepam, escitalopram, rivastigmine, betahistine, sumatriptan, atomoxetine, ibuprofen, pregabalin, acetylcysteine, montelukast, rupatadine, simethicone, pantoprazole, ranitidine, metformin, atorvastatin, acetylsalicylic acid, alendronate sodium, sildenafil and mixture thereof one or more pharmaceutically acceptable alkaline earth metal carbonates in an amount from 5 to 35% by weight of the composition; particularly calcium carbonate, one or more pharmaceutically acceptable acids in an amount from 10 to 65% by weight of the composition; particularly citric acid, maleic acid or mixture thereof, one or more lubricants in an amount from 1 to 10% by weight; polyethylene glycol (PEG6000 and PEG4000), magnesium stearate, leucine, sodium benzoate, sodium lauryl sulphate or mixture thereof and optionally one or more additional pharmaceutically acceptable excipients or carriers, being the sum of ingredients 100%.

In an embodiment, the composition of the present invention comprises:

a therapeutically effective amount of an active pharmaceutical ingredient; selected from the group consisting of levetiracetam, brivaracetam, lacosamide, paracetamol, diltiazem, memantine, quetiapine, donepezil, apixaban, bilastine, diazepam, escitalopram, rivastigmine, betahistine, sumatriptan, atomoxetine, ibuprofen, pregabalin, acetylcysteine, montelukast, rupatadine, simethicone, pantoprazole, ranitidine, metformin, atorvastatin, acetylsalicylic acid, alendronate sodium, sildenafil and mixture thereof one or more pharmaceutically acceptable alkaline earth metal carbonates in an amount from 10 to 35% by weight of the composition; particularly calcium carbonate, one or more pharmaceutically acceptable acids in an amount from 30 to 65% by weight of the composition; particularly citric acid, maleic acid or mixture thereof, one or more lubricants in an amount from 1 to 10% by weight; polyethylene glycol (PEG6000 and PEG4000), magnesium stearate, leucine, sodium benzoate, sodium lauryl sulphate or mixture thereof and optionally one or more additional pharmaceutically acceptable excipients or carriers, being the sum of ingredients 100%.

In an embodiment, the composition of the present invention comprises:

a therapeutically effective amount of an active pharmaceutical ingredient; selected from the group consisting of levetiracetam, brivaracetam, lacosamide, paracetamol, diltiazem, memantine and mixture thereof one or more pharmaceutically acceptable alkaline earth metal carbonates in an amount from 1 to 35% by weight of the composition; particularly calcium carbonate, one or more pharmaceutically acceptable acids in an amount from 2 to 65% by weight of the composition; particularly citric acid, maleic acid or mixture thereof, one or more lubricants in an amount from 1 to 10% by weight; particularly polyethylene glycol (PEG6000), magnesium stearate, leucine or mixture thereof and optionally one or more additional pharmaceutically acceptable excipients or carriers, being the sum of ingredients 100%.

In an embodiment, the composition of the present invention comprises:

a therapeutically effective amount of an active pharmaceutical ingredient; selected from the group consisting of levetiracetam, brivaracetam, lacosamide, paracetamol, diltiazem, memantine and mixture thereof one or more pharmaceutically acceptable alkaline earth metal carbonates in an amount from 5 to 35% by weight of the composition; particularly calcium carbonate, one or more pharmaceutically acceptable acids in an amount from 10 to 65% by weight of the composition; particularly citric acid, maleic acid or mixture thereof, one or more lubricants in an amount from 1 to 10% by weight; particularly polyethylene glycol (PEG6000), magnesium stearate, leucine or mixture thereof and optionally one or more additional pharmaceutically acceptable excipients or carriers, being the sum of ingredients 100%.

In an embodiment, the composition of the present invention comprises:

a therapeutically effective amount of an active pharmaceutical ingredient; selected from the group consisting of levetiracetam, brivaracetam, lacosamide, paracetamol, diltiazem, memantine and mixture thereof one or more pharmaceutically acceptable alkaline earth metal carbonates in an amount from 10 to 35% by weight of the composition; particularly calcium carbonate, one or more pharmaceutically acceptable acids in an amount from 30 to 65% by weight of the composition; particularly citric acid, maleic acid or mixture thereof, one or more lubricants in an amount from 1 to 10% by weight; particularly polyethylene glycol (PEG6000), magnesium stearate, leucine or mixture thereof and optionally one or more additional pharmaceutically acceptable excipients or carriers, being the sum of ingredients 100%.

In an embodiment, the composition of the invention is an effervescent composition selected from effervescent powder, effervescent granules, effervescent pellets and effervescent tablets. In an embodiment, the composition of the invention is an effervescent tablet. All embodiments disclosed for the composition of the effervescent solid pharmaceutical composition (taken them alone or in combination with other embodiments disclosed above or below) disclosed in the present invention also apply to the effervescent tablet.

In an embodiment, the composition of the invention is an effervescent tablet selected from the group consisting of direct compression effervescent tablet and granulation effervescent tablet. In an embodiment, the composition of the invention is a granulation effervescent tablet selected from dry granulation, wet granulation and Moisture Activated Dry Granulation (MADG); particularly dry granulation and Moisture Activated Dry Granulation.

Commonly, the combination of excipients of the compositions can modify some physical parameters of the composition such as for example hardness and disintegration. Hardness of tablets is important for carrying tablets without any breaking and using them safely; disintegration is also important for dispersing rapidly, in the case of effervescent product de disintegration if performed by effervescence upon contact with water and getting the product ready for use in a short time. As the tablet gets harder, the fragility becomes lower but this effect the effervescent time becoming slower. In particular, the effervescent solid compositions of the present invention do not break during the preparation process and carrying; and also disintegrate in water rapidly by effervescence.

In an embodiment, the composition of the invention is a tablet having a hardness from 15 to 140 N; particularly from 15 to 70 N, more particularly from 15 to 40N, much more particularly from 20 to 35N.

In an embodiment, the composition of the invention is a tablet having a residual humidity equal to or lower than 2% in relation to the total weight of the composition.

It is also part of the invention a process for the preparation of the compositions of the present invention.

The appropriate process can readily be determined by those skilled in the art according to the type of formulation being prepared. All embodiments disclosed for the composition of the invention, also apply to their preparation processes.

In an embodiment, the effervescent solid compositions of the present invention are effervescent powder. For example, the process comprises: (a) mixing the suitable excipients with the pharmaceutically active ingredient; and (b) optionally lubricating the mixture obtained in step (a).

In an embodiment, the effervescent solid compositions of the present invention are effervescent granules. For example, the process comprises preparing a granulating suspension of the active ingredient in a suitable solvent and optionally other suitable excipients by sieving the wet active ingredient through a sieve having an appropriate light sieve; drying wet suspension obtained in previous step; and sieving the dry granulate obtained in previous step through a sieve having an appropriate light sieve.

Other alternative process for the preparation of granules comprises mixing water with the active ingredient and knead in a mortar; sieving through a sieve having an appropriate light sieve; dry the mixture obtained in previous step; and sieving through a sieve having an appropriate light sieve.

In an embodiment, the effervescent solid composition of the present invention is an effervescent tablet. Any method for the preparation of direct compression tablets or granulation tablets disclosed in the state of the art can be used for the preparation of the present invention as it is shown in the experimental data (cf. section 2.1.2.). Particularly, the dry granulation tablets of the present invention can be prepared by the commonly used dry granulation process and also by a moisture activated dry granulation (abbreviated as MADG) process or a moisture effervescent activated dry granulation (abbreviated as MEDG) process.

In an embodiment, the effervescent solid composition of the present invention is a direct compression tablet. For example, the process for the preparation of the direct compression tablets of the invention comprises the following steps:

(c) mixing the suitable excipients with the pharmaceutically active ingredient;

(d) optionally lubricating the mixture obtained in step (c); and (e) compressing the mixture obtained in step (d) with a suitable punch to yield a direct compression composition of the present invention.

In an embodiment, the process for preparing the direct compression tablets of the present invention comprises the following steps:

(f) mixing diluent(s) with the pharmaceutically active ingredient and optionally other suitable excipients;

(g) optionally lubricating the mixture obtained in step (f); and (h) compressing the mixture obtained in step (g) with a suitable punch to yield a direct compression composition of the present invention.

In an embodiment, the effervescent solid composition of the present invention is a granulation tablet.

In an embodiment, the effervescent solid composition of the present invention is a dry granulation tablet. In an embodiment, the process for the preparation of dry granulation tablets of the invention comprises the following steps:

(i) preparing the granulated active ingredient;

(j) mixing the suitable excipients with the granulated active ingredient obtained in step (i);

(k) optionally lubricating the mixture obtained in step (j); and (l) compressing the mixture obtained in step (k) with a suitable punch to yield a dry-granulation compression composition of the present invention.

In an embodiment, the process for preparing the dry granulation compression tablets of the present invention comprises the following steps:

(m) preparing the granulated active ingredient by:

(m1) compacting the active ingredient and optionally other suitable excipients;

(m2) sieving the compacted mixture obtained in step (m1) through a sieve having an appropriate light sieve;

(n) mixing the suitable excipients with the granulated active ingredient obtained in step (m);

(p) optionally lubricating the mixture obtained in step (n); and (q) compressing the mixture obtained in step (q) with a suitable punch to yield a dry-granulation compression composition of the present invention.

In an embodiment, the effervescent solid composition of the present invention is a Moisture Activated Dry Granulation tablet (MADG). In an embodiment, the process for the preparation of MADG tablets of the present invention comprises the following steps:

(m") preparing the granulated active ingredient by mixing the active ingredient with water in an amount from 1 to 4% by weight and optionally other suitable excipients;

(n) mixing the suitable excipients with the granulated active ingredient obtained in step (m");

(p) optionally lubricating the mixture obtained in step (n); and (q) compressing the mixture obtained in step (q) with a suitable punch to yield a dry-granulation compression composition of the present invention.

In an embodiment, step (m") of the process for the preparation of MADG tablets of the present invention comprises pulverizing the water onto the active ingredient and optionally other suitable excipients.

In an embodiment, the effervescent solid composition of the present invention is a Wet granulation tablet. In an embodiment, the process for preparing the wet granulation compression tablets of the present invention comprises the following steps:

(m') preparing the granulated active ingredient by:

(m1') preparing a granulating suspension of the active ingredient in one or more suitable organic solvents and optionally other suitable excipients;

(m2') sieving the wet active ingredient through a sieve having an appropriate light sieve;

(m3') drying the active ingredient obtained in step (m2'); and (m4') sieving the dry active ingredient obtained in step (m3') through a sieve having an appropriate light sieve.

(n') mixing the suitable excipients with the granulated active ingredient obtained in step (m');

(p') optionally lubricating the mixture obtained in step (n'); and (q') compressing the mixture obtained in step (q') with a suitable punch to yield a wet-granulation compression composition of the present invention.

In an embodiment, the process for preparing the wet granulation compression tablets of the present invention comprises the following steps:

(r) preparing a first granulate comprising the one or more pharmaceutically acceptable alkaline earth metal carbonates or hydrogencarbonates as defined in the present invention following the process as defined above; and optionally the active ingredient;

(s) preparing a second granulate comprising the one or more pharmaceutically acceptable acids, pharmaceutically acceptable acid salts, or alternatively, a mixture thereof as defined in the present invention following the process as defined above; and optionally the active ingredient;

(n") mixing the suitable excipients with the first granulate obtained in step (r); and the second granulate obtained in step (s); and optionally the active ingredient;

(p') optionally lubricating the mixture obtained in step (n'); and (q') compressing the mixture obtained in step (q') with a suitable punch to yield a wet-granulation compression composition of the present invention.

In an embodiment, the appropriate solvent of granulating steps of the processes as defined above are selected from the group consisting of water, soluble organic solvents such as alcohols selected from ethanol and isopropanol, and a mixture thereof.

Another aspect of the invention relates to a composition of the present invention as defined above for use as a medicament. In an embodiment, the composition of the present invention as defined above when the active ingredient is levetiracetam for use in the treatment of partial onset seizures. This aspect could be also formulated as the use of the composition of the invention which comprises levetiracetam as defined above for the preparation of a medicament for the treatment of partial onset seizures. It also relates to a method for the treatment of a mammal suffering from partial onset seizures, wherein the method comprises administering to said mammal the composition of the present invention as defined above. In an embodiment, the composition of the present invention as defined above when the active ingredient is brivaracetam for use in the treatment of partial onset seizures. This aspect could be also formulated as the use of the composition of the invention which comprises brivaracetam as defined above for the preparation of a medicament for the treatment of partial onset seizures. It also relates to a method for the treatment of a mammal suffering from partial onset seizures, wherein the method comprises administering to said mammal the composition of the present invention which comprises brivaracetam as defined above. In an embodiment, the composition of the present invention as defined above when the active ingredient is lacosamide for use in the treatment of partial onset seizures. This aspect could be also formulated as the use of the composition of the invention which comprises lacosamide as defined above for the preparation of a medicament for the treatment of partial onset seizures. It also relates to a method for the treatment of a mammal suffering from partial onset seizures, wherein the method comprises administering to said mammal the composition of the present invention which comprises lacosamide as defined above. In an embodiment, the composition of the present invention as defined above when the active ingredient is paracetamol for use in the treatment of pain and fever. This aspect could be also formulated as the use of the composition of the invention which comprises paracetamol as defined above for the preparation of a medicament for the treatment of pain and fever. It also relates to a method for the treatment of a mammal suffering from pain and fever, wherein the method comprises administering to said mammal the composition of the present invention which comprises paracetamol as defined above. In an embodiment, the composition of the present invention as defined above when the active ingredient is diltiazem for use in the treatment of high blood pressure, angina, heart arrhythmias, and hyperthyroidism. This aspect could be also formulated as the use of the composition of the invention which comprises diltiazem as defined above for the preparation of a medicament for the treatment of high blood pressure, angina, heart arrhythmias, and hyperthyroidism. It also relates to a method for the treatment of a mammal suffering from high blood pressure, angina, heart arrhythmias, and hyperthyroidism, wherein the method comprises administering to said mammal the composition of the present invention which comprises diltiazem as defined above. In an embodiment, the composition of the present invention as defined above when the active ingredient is memantine for use in the treatment of Alzheimer's disease. This aspect could be also formulated as the use of the composition of the invention which comprises memantine as defined above for the preparation of a medicament for the treatment of Alzheimer's disease. It also relates to a method for the treatment of a mammal suffering from Alzheimer's disease, wherein the method comprises administering to said mammal the composition of the present invention which comprises memantine as defined above.

Compositions of the present invention as defined above are particularly indicated for chronic diseases due to being essentially free of sodium and having a low content of alkaline earth metal such as calcium and magnesium. Then, another embodiment of this aspect of the invention relates to compositions of the present invention as defined above for use in the treatment of chronic diseases. In a preferred embodiment, the chronic disease is but not limited to epilepsy; thromboembolic disorders; psychotic disorders such as schizophrenia or bipolar disorder; neurodegenerative disorders such as Parkinson or Alzheimer disease; allergic disorders such as allergic rhinitis; vertigo associated disorders; osteoporosis; and chronic pain.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples are provided by way of illustration, and they are not intended to be limiting of the present invention. Furthermore, the present invention covers all possible combinations of particular and preferred embodiments described herein.

EXAMPLES

1. General Consideration

Method for the measurement of the effervescent time of the compositions of the invention according to the disintegration test for effervescent tablets of the Ph. Eur. 9.8 online version for effervescent tablet which implies:

DEFINITION: Effervescent tablets are uncoated tablets generally containing acid substances and carbonates or hydrogen carbonates, which react rapidly in the presence of water to release carbon dioxide. They are intended to be dissolved or dispersed in water before administration.

TESTS: Disintegration. Place 1 tablet in a beaker containing 200 mL of water R at 15-25° C.; numerous bubbles of gas are evolved. When the evolution of gas around the tablet or its fragments ceases the tablet has disintegrated, being either dissolved or dispersed in the water so that no agglomerates of particles remain. Repeat the operation on 5 other tablets. The tablets comply with the test if each of the 6 tablets used disintegrates in the manner prescribed within 5 min, unless otherwise justified and authorized.

2. Solid Pharmaceutical Compositions 2.1. Effervescent Compositions of the Present Invention 2.1.1. Compositions Comprising Levetiracetam The qualitative and quantitative composition of the effervescent compositions in form of tablets or powder of the present invention are shown in Table 1, wherein the amount of each of the components are expressed in weight percent:

TABLE 1

| Function | Name | Examples (% w/w) | | | | | | | | |
| --- | --- | --- | --- | --- | --- | --- | --- | --- | --- | --- |
| | | Ex. 1 | Ex. 2 | Ex. 3 | Ex. 4 | Ex. 5 | Ex. 6 | Ex. 7 | Ex. 8 | Ex. 16 |
| Active ingredient | levetiracetam | 25 | 25 | 25 | 25 | 25 | 40[a] | 40 | 40 | 40 |
| Diluent | Mannitol [b] | 40 | — | — | — | — | — | — | — | — |
| | Isomalt 721 | — | 46 | 44 | 39.4 | 40 | 18 | 12.48 | 12.48 | 23.48 |
| Alkaline earth metal carbonate (base) | CaCO$_3$ | 10 | 7 | 8 | 8 | 8 | 12 | 12 | 12 | — |
| | MgCO$_3$ | — | — | — | — | — | — | — | — | 6 |
| Acid | Citric Acid anhydrous | 15 | — | — | — | — | — | 1 | — | — |
| | Maleic acid | — | 12 | — | 18 | 16 | 24 | 26 | 27 | 22 |
| | Glycine hydrochloride | — | — | 14 | — | — | — | — | — | — |
| | Malic acid | — | — | — | — | 4 | — | — | — | — |
| Disintegrant | Crospovidone | 4 | — | — | — | — | — | — | — | — |
| Lubricant | PEG 6000 | 5 | 2 | 2 | 2 | — | — | — | — | — |
| | Magnesium stearate | 1 | — | — | — | — | — | — | — | — |
| | Leucine | — | 8 | 7 | 7 | 7 | 6 | 6 | 6 | 6 |

TABLE 1-continued

| | | Examples (% w/w) | | | | | | | | |
|---|---|---|---|---|---|---|---|---|---|---|
| Function | Name | Ex. 1 | Ex. 2 | Ex. 3 | Ex. 4 | Ex. 5 | Ex. 6 | Ex. 7 | Ex. 8 | Ex. 16 |
| Flavour | Orange flavour | — | — | — | 0.5 | — | — | 1 | 1 | 1 |
| | Tangerine flavour | — | — | — | — | — | — | 0.5 | 0.5 | 0.5 |
| Bitter tastemasking flavours | PureDelivery ™ EverFresh 100 | — | — | — | — | — | — | 0.02 | 0.02 | 0.02 |
| Sweetener | Sucralose | — | — | — | 0.1 | — | — | 1 | 1 | 1 |
| | Total weight of the effervescent acid-base pair | 25 | 19 | 22 | 26 | 28 | 36 | 39 | 39 | 28 |
| | Total weight | 100 | 100 | 100 | 100 | 100 | 100 | 100 | 100 | 100 |

[a] Granulated Levetiracetam prepared from 150 g of levetiracetam and 21 g of purified water (cf. section 2.1.2.3. General process 3 (MEDG))
[b] Mannitol is commercially available with the trademark pearlitol Flash ®

2.1.2. Compositions Comprising Lacosamide

The qualitative and quantitative composition of the tablets of the present invention are shown in Table 2, wherein the amount of each of the components are expressed in weight percent:

TABLE 2

| | | Examples (% w/w) | | | |
|---|---|---|---|---|---|
| Function | Name | Example 9 | Example 10 | Example 11 | Example 12 |
| Active ingredient | lacosamide | 2.5 | 5 | 7.5 | 10 |
| Alkaline earth metal carbonate (base) | CaCO₃ (intragranular) | 10 | 9 | 8 | 7.5 |
| | CaCO₃ (extragranular) | 20 | 20 | 20 | 20 |
| Acid | Citric Acid anhydrous | 60.5 | 59 | 57.5 | 55.5 |
| Binder | Povidone K30 | 1.5 | 1.5 | 1.5 | 1.5 |
| Binding Vehicle | Purified water[c] | q.s. | q.s. | q.s. | q.s. |
| Lubricant | PEG 6000 | 1.5 | 1.5 | 1.5 | 1.5 |
| | Sodium benzoate | 1.5 | 1.5 | 1.5 | 1.5 |
| Flavour | Powdarome Orange Premium | 1.5 | 1.5 | 1.5 | 1.5 |
| Sweetener | Sucralose | 1 | 1 | 1 | 1 |
| | Total weight of the effervescent acid-base pair | 90.5 | 88 | 85.5 | 83 |
| | Total weight | 100 | 100 | 100 | 100 |

[c] Removed during process

2.1.3. Preparation Process

The compositions of the invention of Examples 1-7 defined in Table 1 were prepared following the general processes as defined below using the ingredients and the amounts specified in Table 1.

The composition of the invention of Example 8 was prepared in form of tablets and powder. The tablets of Example 8 were prepared following the general process 2 as defined below using the ingredients and the amounts specified in Table 1. And, the powder of Example 8 was prepared following the general process 2 as defined below, but the mixture obtained in step 7 was introduced in sachets instead of being compressed.

The compositions of the invention Examples 9-12 defined in Table 2 were prepared following the general process 4.

The composition of the invention Example 16 defined in Table 1 was prepared following the general process 2.

2.1.3.1. General Process 1 (Direct Compression)

1. all the components were weighted separately;
2. in case they present agglomerates, sieve separately through an 800 μm mesh sieve;
3. all components were mixed in the tube agitator heidolph at 60 rpm for 5 minutes;
4. in case that the mixture presents agglomerates, sieve through an 800 μm mesh sieve;
5. proceed to direct compression in eccentric machine (Bonals) with 18 mm round flat punches.

The effervescent tablets of Example 1 were prepared following the general process 1.

The effervescent tablets of Examples 2 and 4 were prepared following the general process 1 but adding a grinding up step of the polyethylene glycol in a V-type mixer after step 1.

The effervescent tablets of Example 3 were prepared following the general process 1 but adding a grinding up step of the polyethylene glycol in a V-type mixer after step 1; and mixing in step 4 all the components except from lubricant, flavours and sweetener which are added to the resulting mixture of step 4) maintaining the agitation at 60 rpm for 10 minutes.

The effervescent tablets of Example 5 were prepared following the general process 1 but mixing in step 4 all the components except from lubricant which is added to the resulting mixture of step 4) maintaining the agitation at 60 rpm for 10 minutes.

2.1.3.2. General Process 2 (Direct Compression)

1. all the components were weighted separately;
2. in case they present agglomerates, sieve separately each one through an 800 μm mesh sieve;
3. mix the active ingredient, the diluent, the alkaline earth metal base carbonate and the acid in a V-mixer at 20 rpm for 10 minutes;
4. in case that the mixture presents agglomerates, sieve through an 800 μm mesh sieve;
5. add the flavours, sweeteners and taste masking agent to the previous mixture and mix in a V-mixer at 20 rpm for 10 minutes;
6. add the lubricants to the previous mixture and allow mixing in a V-mixer at 20 rpm for 10 minutes;
7. in case of appearing some agglomerates in the mixture, sieve through an 800 μm mesh sieve;
8. proceed to direct compression in eccentric machine (Bonals) with 25 mm round flat teflon punches.

The effervescent tablets of Example 7 were prepared following the general process 2 but adding the maleic acid in step 3 and the citric acid in step 5 with the flavours, sweeteners and taste masking agent.

The effervescent tablets of Examples 8 were prepared following the general process 2.

2.1.3.3. General Process 3 (MEDG)

A) Preparation of Granulated Active Ingredient:
1. weight all components separately;
2. mix the water with the active ingredient and knead in a V-type mixer;
3. sieve through a 1000 μm mesh sieve;
4. dry at 40° C. for 24 h; and
5. sieve through an 800 μm mesh sieve.

B) Preparation of Tablets from the Granulated Active Ingredient:
1. weight all components and the granulated active ingredient separately;
2. if they present agglomerates, sieve through an 800 μm mesh sieve;

6. Calcium carbonate (extragranular), sucralose, powdarome orange premium, PEG 6000 and sodium benzoate were sifted through ASTM 30#.

7. Sifted ingredients of step 6 were mixed with sized dried granules of step 5 for 30 minutes.

8. Blend of step 7 was compressed using appropriate tooling.

The effervescent tablets of Examples 9-12 were prepared following the general process 4.

2.1.4. Characterization 2.1.4.1. Physical Parameters

The physical paraments of the effervescent tablets of the present invention were calculated. The tablets of the present invention were white round tablets having and homogeneous surface without exfoliation. The physical parameters of the effervescent tablets of the present invention (Examples 1-8) are shown in Table 3:

TABLE 3

| | Examples | | | | | | | | |
| | | | Ex. 3 | | | | | | |
| | Ex. 1 | Ex. 2 | Ex. 3A | Ex. 3B | Ex. 4 | Ex. 5 | Ex. 6 | Ex. 7 | Ex. 8 |
|---|---|---|---|---|---|---|---|---|---|
| Residual humidity[1] | <2% | <2% | <2% | <2% | <2% | <2% | <2% | <2% | <2% |
| Tablet Hardness (N) | — | 94-130 | 60-69/ | 105-123 | 111-125 | — | 60-71 | 26-35 | 35-50 |

[1]The residual humidity is expressed in weight % in relation to the total weight of the effervescent tablet.

3. mix all the components (except lubricant) in biconical mixer at 20 rpm for 10 min;
4. add lubricant to the previous mixture and mix in the biconical mixer at 20 rpm for 10 min;
5. in case of appearing some agglomerates in the mixture, sieve through an 800 μm mesh sieve;
6. proceed to direct compression in eccentric machine (Bonals) with 25 mm round flat teflon punches.

The effervescent tablets of Example 6 were prepared following the general process 3.

2.1.3.4. General Process 4 (Wet Granulation)

1. Lacosamide, citric acid anhydrous, calcium carbonate (intragranular) and povidone K30 were sifted through Vibro-sifter using ASTM 18# sieve and subsequently transferred to Rapid Mixer Granulator.

2. Purified water was taken as a binder vehicle.

3. Ingredients of step 1 were granulated by using the binder vehicle of step 2 (purified water) in order to obtain a wet mass.

4. Wet mass of step 3 was dried in a fluid bed dryer until loss on drying is no more than 0.5% w/w at 75° C.

5. Dried granules as obtained in step 4 were sized through co-mill using 1.5 mm screen.

As it is shown in the values of the physical parameters, the compositions of the present invention (Examples 1-8) have the appropriate hardness and the suitable effervescent time for being used in therapy.

2.1.4.2. Disintegration Test of Effervescent Tablets and Effervescent Powder in Sachets The disintegration test of effervescent tablets and powder prepared in examples 2-8 and 16 was measured as following the disintegration test of effervescent tablets established in the Eur. Ph:

Place one tablet (or powder) in a 250 ml beaker containing 200 ml of water R at 15-25° C. Numerous bubbles of gas are evolved. When the evolution of gas around the tablet (or powder) or its fragments ceases, the tablet should have disintegrated, being either dissolved or dispersed in the water so that no agglomerates remain. Repeat the operation on five additional tablets (or powders from five sachets). The tablets (or powders) comply with the test if each of the six tablets (or powders of each sachets) used in the test disintegrates within 5 minutes, unless otherwise specified in the individual monograph.

The effervescent time value, the pH of the resulting deionized water solution and its visual appearance is summarized in Table 4:

TABLE 4

| Examples | | Effervescent time | pH | Visual appearance of the solution |
|---|---|---|---|---|
| Ex. 2 | | 2 min | 5.6 | Comply with the requirement of the Ph. Eur. (no agglomerates) |
| Ex. 3 | Ex. 3A | 2 min | 6.2 | Comply with the requirement of the Ph. Eur. (no agglomerates) |
| | Ex. 3B | 3 min | 6.2 | Comply with the requirement of the Ph. Eur. (no agglomerates) |
| | Ex. 4 | 1 min 19 seconds | 3.8 | Comply with the requirement of the Ph. Eur. |

TABLE 4-continued

| Examples | Effervescent time | pH | Visual appearance of the solution |
|---|---|---|---|
| Ex. 5 | 1 min | 3.4 | Comply with the requirement of the Ph. Eur. Transparent (without residues) |
| Ex. 6 | 1 min 17 seconds | 4.7 | Comply with the requirement of the Ph. Eur. Transparent (without residues when mixing) |
| Ex. 7 | 1 min 35 seconds | 2.8 | Comply with the requirement of the Ph. Eur. Transparent (without residues when mixing) |
| Ex. 8   Tablets | 2 min | 3 | Comply with the requirement of the Ph. Eur. Transparent (without residues when mixing) |
| sachets | <5 seconds | NA | Comply with the requirement of the Ph. Eur. Transparent (without residues) |
| Ex. 9-12 | <2 min | NA | Comply with the requirement of the Ph. Eur. Transparent (without residues when mixing) |
| Ex. 16 | 50 seconds | NA | Comply with the requirement of the Ph. Eur. Transparent (after few minutes) |

Therefore, the effervescent compositions of the present invention have an effervescent time below 5 minutes rendering a water solution without residues. It means that the compositions of the invention disintegrate quickly and completely upon contact with water evolving carbon dioxide and create a water solution without residues and/or foam having a pleasant taste and thus, improving the compliance of the treatment.

2.1.5. Effervescent Tablets of the Invention Comprising Paracetamol, Diltiazem and Memantine Compositions The qualitative and quantitative composition of the tablets comprising paracetamol, diltiazem and memantine of the present invention are shown in Table 5, wherein the amount of each of the components are expressed in weight percent:

TABLE 5

| | | Examples (% w/w) | | |
|---|---|---|---|---|
| Function | Name | Ex. 13 | Ex. 14 | Ex. 15 |
| Active ingredient | Paracetamol | 35.71 | — | — |
| | Diltiazem | — | 6 | — |
| | memantine | — | — | 6 |
| Diluent | Mannitol [a] | — | — | — |
| | Isomalt 721 | 20.96 | 43 | 43 |
| Alkaline earth metal carbonate (base) | CaCO3 | 10.71 | — | — |
| | MgCO3 | — | 13.5 | 13.5 |
| Acid | Citric Acid anhydrous | — | — | — |
| | Maleic acid | 25.00 | 30 | 30 |
| | Glycine hydrochloride | — | — | — |
| | Malic acid | — | — | — |
| Disintegrant | Crospovidone | — | — | — |
| Lubricant | PEG 6000 | — | — | — |
| | Magnesium stearate | — | — | — |
| | Leucine | 5.36 | 5.6 | 5.6 |
| Flavour | Orange flavour | 0.89 | 0.75 | 0.75 |
| | Tangerine flavour | 0.45 | 0.375 | 0.375 |
| Bitter tastemasking flavours | PureDelivery ™ EverFresh 100 | 0.02 | 0.025 | 0.025 |
| Sweetener | Sucralose | 0.89 | 0.75 | 0.75 |
| | Total weight of the effervescent acid-base pair | 35.71 | 43.50 | 43.50 |
| | Total weight | 100 | 100 | 100 |

[a] Mannitol is commercially available with the trademark pearitol Flash ®

Preparation Process

The composition of the invention of Example 13 defined in Table 5 was prepared following the general process 2 as defined above using the ingredients and the amounts specified in Table 5; but in step 8 the direct compression was performed with 22 mm round flat teflon punches instead of 25 mm.

The composition of the invention of Example 14 defined in Table 5 was prepared following the general process 2 as defined above using the ingredients and the amounts specified in Table 5; but in step 8 the direct compression was performed with 14 mm round flat teflon punches instead of 25 mm.

The composition of the invention of Example 15 defined in Table 5 was prepared following the general process 2 as defined above using the ingredients and the amounts specified in Table 5; but in step 8 the direct compression was performed with 9 mm round flat teflon punches instead of 25 mm.

Characterization—Disintegration Test of Effervescent Tablets

The disintegration test of effervescent tablets prepared in examples 13-15 was measured following the disintegration test of effervescent tablets established in the Eur. Ph as defined above for examples 2-8.

The effervescent time value and the visual appearance of the resulting deionized water solution is summarized in Table 6:

TABLE 6

| Examples | Effervescent time | Visual appearance of the solution |
|---|---|---|
| Ex. 13 | 1 min 58 seconds | Comply with the requirement of the Ph. Eur. |
| Ex. 14 | 2 min 51 seconds | Comply with the requirement of the Ph. Eur. Transparent (without residues) |
| Ex. 15 | 3 min 24 seconds | Comply with the requirement of the Ph. Eur. Transparent |

2.2. Comparative Tablets Falling Outside the Scope of the Present Invention

The comparative tablets comprise all the claimed components. However, at least one of the components are in an amount falling outside the claimed range.

2.2.1. Comparative Compositions Comprising Levetiracetam 2.2.1.1. Comparative Compositions The qualitative and quantitative composition of the comparative tablets of levetiracetam falling outside the scope of the present invention are shown in Table 7, wherein the amount of each of the components are expressed in weight percent:

TABLE 7

| Function | Name | Comparative Examples (% w/w) | | | | |
| | | Comp. Ex. 1 | Comp. Ex. 2 | Comp. Ex. 3 | Comp. Ex. 4 | Comp. Ex. 5 |
|---|---|---|---|---|---|---|
| Active ingredient | levetiracetam | 40.0 | 40.0 | 40.0 | 40.0 | 40.0 |
| Diluent | Isomalt 721 | 38.48 | 23.98 | 49.98 | 38.09 | 44.03 |
| Alkaline earth metal carbonate (base) | CaCO₃ | 12.00 | 0.50 | 0.50 | 12.00 | 6.95 |
| Acid | Maleic acid | 1.00 | 27.00 | 1.00 | 1.39 | 0.50 |
| Lubricant | Leucine | 6.00 | 6.00 | 6.00 | 6.00 | 6.00 |
| Flavour | Orange flavour | 1.00 | 1.00 | 1.00 | 1.00 | 1.00 |
| | Tangerine flavour | 0.50 | 0.50 | 0.50 | 0.50 | 0.50 |
| Bitter tastemasking flavours | PureDelivery ™ EverFresh 100 | 0.02 | 0.02 | 0.02 | 0.02 | 0.02 |
| Sweetener | Sucralose | 1.00 | 1.00 | 1.00 | 1.00 | 1.00 |
| Total weight of the effervescent acid-base pair | | 13.0 | 27.50 | 1.50 | 12.39 | 7.45 |
| Total weight | | 100 | 100 | 100 | | |

2.2.1.2. Preparation Process

The comparative compositions (comp. Ex. 1-5) defined in Table 7 were prepared following the general process 2 (Direct compression) as defined above using the ingredients and the amounts specified in Table 4.

2.2.1.3. Characterization 2.2.1.3.1. Physical Parameters

The physical paraments of the comparative effervescent tablets of levetiracetam falling outside the scope of the present invention were calculated. The comparative tablets (Comparative Examples 1-5) were flat cylindrical white tablets whose physical parameters are shown in Table 8.

TABLE 8

| | Comp. Ex. 1 | Comp. Ex. 2[(1)] | Comp. Ex. 3 | Comp. Ex. 4 | Comp. Ex. 5 |
|---|---|---|---|---|---|
| Weight mean (g) | 2.521 | 2.4843 | 2.5129 | 2.5320 | 2.5150 |
| Hardness mean (N) | 42.2 | 39.2 | 42.9 | 39.5 | 42.4 |
| Aspect | homogeneous surface and imperceptible exfoliation | inhomogeneous surface and exfoliation | homogeneous surface and imperceptible exfoliation | homogeneous surface and imperceptible exfoliation | homogeneous surface and imperceptible exfoliation. |

[(1)]Adherences to the punches are generated affecting the compression process 2.2.1.3.2. Disintegration Test of Effervescent Tablets The disintegration test of the comparative effervescent tablets of levetiracetam prepared in comparative examples 1-5 was measured as following the disintegration test of effervescent tablets established in the Eur. Ph as defined above.

The effervescent time value and its visual appearance is summarized in Table 9:

TABLE 9

| Examples | Effervescent time | Visual appearance of the solution |
|---|---|---|
| Comp. Ex. 1 | Greater than 15 min | The solution is not transparent and presents residues floating |
| Comp. Ex. 2 | Greater than 15 min | The solution is not transparent and presents residues floating |

TABLE 9-continued

| Examples | Effervescent time | Visual appearance of the solution |
|---|---|---|
| Comp. Ex. 3 | Greater than 15 min | The solution is transparent but it presents bottom or floating residues |
| Comp. Ex. 4 | Greater than 15 min | The solution is not transparent and presents residues floating |
| Comp. Ex. 5 | Greater than 15 min | The solution is transparent and it does not present residues. |

Therefore, the comparative effervescent compositions of levetiracetam falling outside the present invention do not have an effervescent time below 5 minutes rendering a water solution without residues. It means that the comparative compositions 1-5 disintegrate slowly and/or not completely upon contact with water evolving carbon dioxide and create a water solution with residues and/or foam, having a bad taste and thus, reducing the compliance of the treatment.

2.2.2. Comparative Compositions Comprising Lacosamide 2.2.2.1. Comparative Compositions The qualitative and quantitative composition of the comparative tablets of lacosamide (comparative Example 6-7) falling outside the scope of the present invention are shown in Table 10, wherein the amount of each of the components are expressed in weight percent:

TABLE 10

| Function | Name | Examples (% w/w) Comp. Ex. 6 | Comp. Ex. 7 |
|---|---|---|---|
| Active ingredient | lacosamide | 10 | 10 |
| Alkaline earth metal | CaCO₃ (intragranular) | 62 | 0.25 |
| carbonate (base) | CaCO₃ (extragranular) | 20 | 0.25 |
| Acid | Citric Acid anhydrous | 1 | 82.5 |
| Binder | Povidone K30 | 1.5 | 1.5 |
| Binding Vehicle | Purified water⁽ᶜ⁾ | q.s. | q.s. |
| Lubricant | PEG 6000 | 1.5 | 1.5 |
| | Sodium benzoate | 1.5 | 1.5 |
| Flavour | Powdarome Orange Premium | 1.5 | 1.5 |
| Sweetener | Sucralose | 1 | 1 |
| Total weight of the effervescent acid-base pair | | 83 | 83 |
| Total weight | | 100 | 100 |

(b) Removed during process

2.2.2.2. Preparation Process

The comparative compositions (comp. Ex. 6 and 7) defined in Table 10 were prepared following the general process 4 (Wet Granulation) as defined above using the ingredients and the amounts specified in Table 10, but in step 5 dried granules as obtained in step 4 were sized through co-mill using 1.0 mm screen; and in step 6 calcium carbonate (extragranular), sucralose and powdarome orange premium were sifted through ASTM 18# and PEG 6000 and sodium benzoate were sifted through ASTM 40#.

2.2.2.3. Characterization

2.2.2.3.1. Physical Parameters

The physical paraments of the comparative effervescent tablets of lacosamide falling outside the scope of the present invention were calculated. The physical parameters of comparative Examples 6-7 are shown in Table 11.

TABLE 11

| | Comp. Ex. 6 | Comp. Ex. 7 |
|---|---|---|
| Average Weight (mg) | 2005.3 mg | 2001.7 mg |
| Uniformity of Weight (mg) | Min: 1989 mg Max: 2012 mg | Min: 1992 mg Max: 2008 mg |

TABLE 11-continued

| | Comp. Ex. 6 | Comp. Ex. 7 |
|---|---|---|
| Thickness (mm) | 4.20-4.27 mm | 4.18-4.26 mm |
| Resistance to crushing (N) ⁽¹⁾ | 49 N-61 N | 45 N-58 N |

⁽¹⁾ Resistance to crushing was performed according to by European Pharmacopoeia 6ᵗʰ edition, volume 1, Monography 2.9.8.

2.2.2.3.2. Disintegration Test of Effervescent Tablets

The disintegration test of the comparative effervescent tablets of lacosamide prepared in comparative examples 6-7 was measured as following the disintegration test of effervescent tablets established in the Eur. Ph as defined above.

The effervescent time value and its visual appearance is summarized in Table 12:

TABLE 12

| Examples | Effervescent time | Visual appearance of the solution |
|---|---|---|
| Comp. Ex. 6 | Greater than 5 min | The solution is not transparent and presents residues (agglomerate) floating |
| Comp. Ex. 7 | Greater than 5 min | The solution is not transparent and presents residues (agglomerate) floating |

Therefore, the comparative effervescent compositions of lacosamide falling outside the present invention do neither have an effervescent time below 5 minutes rendering a water solution without residues. It means that the comparative compositions 6-7 disintegrate slowly and not completely upon contact with water evolving carbon dioxide and create a water solution with residues and/or foam, having a bad taste and thus, reducing the compliance of the treatment.

2.2. Additional Compositions of the Invention (Examples 17-42)

Composition

The qualitative and quantitative composition of the tablets of Examples 17-42 comprising brivaracetam, quetiapine, memantine, donepezil, apixaban, bilastine, diazepam, escitalopram, rivastigmine, betahistine, sumatriptan, atomoxetine, ibuprofen, pregabalin, acetylcysteine, montelukast, rupatadine, simethicone, pantoprazole, ranitidine, metformin, atorvastatin, acetylsalicylic acid, alendronate sodium, sildenafil and of the present invention are shown in Table 13, wherein the amount of each of the components are expressed in weight percent:

TABLE 13

| Function | Name | Examples (% w/w) Ex. 17 | Ex. 18 | Ex. 19 | Ex. 20 | Ex. 21 | Ex. 22 |
|---|---|---|---|---|---|---|---|
| Active ingredient | Non-proprietary name | quetiapine | brivaracetam | memantine | donepezil | apixaban | bilastine |
| | amount | 12.50 | 6.25 | 6.66 | 3.33 | 1.66 | 6.66 |
| Diluent | Mannitol ⁽ᵃ⁾ | — | — | — | — | — | — |
| | Isomalt 721 | 23.75 | 28.75 | 23.33 | 26.66 | 28.33 | 26.66 |
| Alkaline earth metal carbonate (base) | CaCO₃ | 16.25 | 16.87 | 17.63 | 17.63 | 17.63 | 17.63 |
| | MgCO₃ | — | — | — | — | — | — |
| Acid | Citric Acid anhydrous | — | — | — | — | — | — |
| | Maleic acid | 37.50 | 38.75 | 40 | 40 | 40 | 36.66 |
| | Glycine hydrochloride | — | — | — | — | — | — |
| | Malic acid | — | — | — | — | — | — |
| Disintegrant | Crospovidone | — | — | — | — | — | — |
| Lubricant | PEG 6000 | — | — | — | — | — | — |
| | Magnesium stearate | — | — | — | — | — | — |
| | Leucine | 7.5 | 7 | 8.33 | 8.33 | 8.33 | 8.33 |

TABLE 13-continued

| Flavour | Orange flavour | 1 | 0.93 | 1.66 | 1.66 | 1.66 | 1.66 |
|---|---|---|---|---|---|---|---|
| | Tangerine flavour | 0.5 | 0.46 | 0.66 | 0.66 | 0.66 | 0.66 |
| Bitter tastemasking flavours | PureDelivery™ EverFresh 100 | 0.025 | 0.031 | 0.033 | 0.033 | 0.033 | 0.033 |
| Sweetener | Sucralose | 0.975 | 0.938 | 1.66 | 1.66 | 1.66 | 1.66 |
| | Total weight of the effervescent acid-base pair | 53.75 | 55.62 | 57.63 | 57.63 | 57.63 | 54.30 |
| | Total weight | 100 | 100 | 100 | 100 | 100 | 100 |

| | | Examples (% w/w) | | | | | |
|---|---|---|---|---|---|---|---|
| Function | Name | Ex. 23 | Ex. 24 | Ex. 25 | Ex. 26 | Ex. 27 | Ex. 28 |
| Active ingredient | Non-proprietary name | diazepam | escitalopram | rivastigmine | betahistine | sumatriptan | atomoxetine |
| | amount | 5 | 4 | 2 | 4 | 10 | 16 |
| Diluent | Tabletose | | | 40 | | | |
| | Ludipress | | | | | 30 | |
| | Perlitol | | | | | | 23.4 |
| | Lactose Fast Flo | | | | 46 | | |
| | Isomalt 721 | 35 | 36 | | | | |
| Alkaline earth metal carbonate (base) | CaCO₃ | 13.4 | 13.4 | 10.83 | 9.25 | 13.4 | 14 |
| Acid | Maleic acid | 30 | 30 | 24.33 | 20 | 30 | 30 |
| Lubricant | PEG 6000 | 0.56 | | | 0.7 | | 6 |
| | PEG 4000 | | 0.56 | | | 6 | |
| | Sodium Lauryl sulfate | | | | | 0.56 | |
| | Leucine | 6 | 6 | 10 | 7.5 | | |
| Flavour | Orange flavour | 4 | 4 | | 5 | 4 | 4 |
| | Tangerine flavour | 2 | 2 | | 2.5 | 2 | 2.56 |
| | Apple flavour | | | 6.83 | | | |
| Bitter tastemasking flavours | PureDelivery™ EverFresh 100 | 0.04 | 0.04 | 0.07 | 0.05 | 0.04 | 0.04 |
| Sweetener | Sucralose | 4 | 4 | 5.93 | 5 | 4 | 4 |
| | Total weight of the effervescent acid-base pair | 43.4 | 43.4 | 35.17 | 29.25 | 43.4 | 44 |
| | Total weight | 100 | 100 | 100 | 100 | 100 | 100 |

| | | Examples (% w/w) | | | | | |
|---|---|---|---|---|---|---|---|
| Function | Name | Ex. 29 | Ex. 30 | Ex. 31 | Ex. 32 | Ex. 33 | Ex. 34 |
| Active ingredient | Non-proprietary name | ibuprofen | pregabalin | acetylcysteine | montelukast | rupatadine | simethicone |
| | amount | 25 | 15 | 25 | 2.5 | 2.5 | 12 |
| Diluent | Xilitab | | | | 44.75 | | |
| | Xiliisol | | | | | 44.75 | |
| | Isomalt 721 | 20.83 | 30 | 20.83 | | | 30 |
| Alkaline earth metal carbonate (base) | CaCO₃ | 11.58 | 11.4 | 11.25 | 12.5 | 12.5 | 13.15 |
| Acid | Citric Acid anhydrous | | 27.5 | | | | |
| | Malic acid | 25 | | | | | 28.75 |
| | Glycine hydrochloride | 8.33 | 5 | 8.33 | | 30 | 5 |
| | Fumaric acid | | | 25.33 | | | |
| | Tartaric acid | | | | 30 | | |
| Lubricant | PEG 6000 | 0.22 | 0.41 | | | | 7.5 |
| | Sodium Lauryl sulfate | | | 0.18 | | | |
| | Leucine | 6.25 | 7.5 | 6.25 | 2.5 | 2.5 | |
| Flavour | Orange flavour | | 1.25 | 1.13 | 2.6 | 2.6 | |
| | Tangerine flavour | | 0.63 | 0.52 | 2.5 | 2.5 | |
| | Apple flavour | 1.69 | | | | | 1.79 |

47 48

TABLE 13-continued

| Bitter tastemasking flavours | PureDelivery™ EverFresh 100 | 0.02 | 0.03 | 0.02 | 0.05 | 0.05 | 0.03 |
|---|---|---|---|---|---|---|---|
| Sweetener | Sucralose | 1.08 | | 1.16 | 2.6 | 2.6 | 1.79 |
| | Aspartame | | 1.29 | | | | |
| Total weight of the effervescent acid-base pair | | 44.92 | 43.9 | 44.92 | 42.5 | 42.5 | 46.9 |
| Total weight | | 100 | 100 | 100 | 100 | 100 | 100 |

| | | Examples (% w/w) | | | | | |
|---|---|---|---|---|---|---|---|
| Function | Name | Ex. 35 | Ex. 36 | Ex. 37 | Ex. 38 | Ex. 39 | Ex. 40 |
| Active ingredient | Non-proprietary name | pantoprazole | ranitidine | metformin | atorvastatin | acetylsalicylic acid | alendronate sodium |
| | amount | 8 | 15 | 35.71 | 16 | 23.81 | 14 |
| Diluent | Xilitab | | | 17.86 | | 23.81 | |
| | Perlitol | | 30 | | 24 | | |
| | Isomalt 721 | 32 | | | | | 26.4 |
| Alkaline earth metal carbonate (base) | $CaCO_3$ | 13.4 | 11.4 | 10.71 | 13.4 | 10.86 | 13.4 |
| Acid | Maleic acid | 30 | 27.5 | 22.29 | | 26.19 | 30 |
| | Glycine hydrochloride | | 5 | 5.36 | | 4.76 | |
| | Glutamic acid hydrochloride | | | | 30 | | |
| Disintegrant | Povidone | | | | | 0.39 | |
| Lubricant | PEG 6000 | 6 | 0.11 | 0.08 | | | |
| | Leucine | | 7.8 | 5.71 | 6 | 7.14 | 6 |
| Flavour | Orange flavour | 4.56 | 1.25 | | 4.56 | 1.19 | 4 |
| | Tangerine flavour | 2 | 0.63 | | 2 | 0.6 | 2 |
| | Apple flavour | | | 1.34 | | | |
| Bitter tastemasking flavours | PureDelivery™ EverFresh 100 | 0.04 | 0.03 | 0.02 | 0.04 | 0.3 | 0.04 |
| Sweetener | Sucralose | 4 | 1.29 | 0.92 | 4 | 1.22 | 4.16 |
| Total weight of the effervescent acid-base pair | | 43.4 | 32.5 | 38.36 | 43.4 | 41.81 | 43.4 |
| Total weight | | 100 | 100 | 100 | 100 | 100 | 100 |

| | | Examples (% w/w) | |
|---|---|---|---|
| Function | Name | Ex. 41 | Ex. 42 |
| Active ingredient | Non-proprietary name | sildenafil | Apixaban |
| | amount | 5 | 1.67 |
| Diluent | Adventose | 20 | |
| | Isomalt 721 | | 43.33 |
| Alkaline earth metal carbonate (base) | $MgCO_3$ | 16.75 | 11.33 |
| Acid | Maleic acid | 37.5 | 27.67 |
| Lubricant | Leucine | 8 | 8.33 |
| Flavour | Orange flavour | 5.2 | |
| | Tangerine flavour | 2.5 | |
| | Apple flavour | | 2.33 |
| Bitter tastemasking flavours | PureDelivery™ EverFresh 100 | 0.05 | 0.07 |
| Sweetener | Sucralose | 5 | 5.27 |
| Total weight of the effervescent acid-base pair | | 54.25 | 39 |
| Total weight | | 100 | 100 |

All the compositions of the invention of examples 1-42 specifically contain an amount of calcium that is equal to or less than 180 mg of calcium, and an amount of Magnesium that is equal to or less than 50 mg.

Preparation Process

The compositions of the invention of Example 17-42 defined in Table 13 are prepared following the general processes 1 or 2 as defined above using the ingredients and the amounts specified in Table 13.

CITATION LIST

1. EMA/CHMP/338679/2014
2. George, J. et al. The Association of Cardiovascular Events with Sodium-Containing Effervescent, Dispersible and Soluble Medications; Nested Case-control Study, B M J, 2013; 347: f6954
3. WO2015/040460
4. EP1837019
5. WO00/28973
6. EP1067904
7. EP1837019
8. WO00/28973
9. Meier, C. et al. Antiepileptics and Bone Health, Ther. Adv. Musculoskelet. Dis., 2011, 3(5), pp. 235-243.

The invention claimed is:

1. An effervescent solid pharmaceutical composition comprising:

an active pharmaceutical ingredient, wherein the active pharmaceutical ingredient is lacosamide;

one or more of a pharmaceutically acceptable alkaline earth metal carbonate or hydrocarbonate thereof in an amount in a range from 1 to 31% by weight of the composition, wherein the one or more of the pharmaceutically acceptable alkaline earth metal carbonate or hydrocarbonate thereof comprise calcium carbonate or magnesium carbonate;

one or more of a pharmaceutically acceptable acid, a salt thereof, or a mixture thereof, in an amount in a range from 2 to 62% by weight of the composition, wherein the one or more of the pharmaceutically acceptable acid, the salt thereof, or the mixture thereof is at least one material selected from the group consisting of citric acid, malic acid, glycine hydrochloride, fumaric acid, tartaric acid, and glutamic acid; and one or more of a pharmaceutically acceptable excipient or a pharmaceutically acceptable carrier, wherein a total content of an ion sodium in the effervescent solid pharmaceutical composition is equal to or lower than 1 mmol, wherein a molar ratio between the one or more of the pharmaceutically acceptable acid, the salt thereof, or the mixture thereof, and the one or more of the pharmaceutically acceptable alkaline earth metal carbonate or hydrocarbonate thereof, is in a range from 1.05:1 to 1.07:1, and wherein the effervescent solid pharmaceutical composition is provided in a tablet formulation.

2. The effervescent solid pharmaceutical composition according to claim 1, wherein a disintegration time of the tablet formulation is equal to or less than 5 minutes, when the disintegration time is measured using a disintegration test of effervescent tablets established in the European Pharmacopoeia (Ph. Eur.), which comprises placing a tablet in a 250 mL beaker containing 200 mL of water R at 15-25° C., leaving numerous bubbles of a gas to evolve, and measuring a time when an evolution of the gas around the tablet or fragments thereof ceases and the tablet has disintegrated, being either dissolved or dispersed in the water so that no agglomerates remain.

3. The effervescent solid pharmaceutical composition according to claim 1, wherein the composition is free of sodium.

4. The effervescent solid pharmaceutical composition according to claim 1, wherein the active pharmaceutical ingredient is in a range from 0.5% to 60% by weight of the composition.

5. The effervescent solid pharmaceutical composition according to claim 1, wherein the amount of the one or more of the pharmaceutically acceptable alkaline earth metal carbonate or hydrocarbonate thereof is in a range from 2 to 28% by weight of the composition, and the amount of the one or more of the pharmaceutically acceptable acid, the salt thereof, or the mixture thereof is in a range from 4 to 56% by weight of the composition.

6. The effervescent solid pharmaceutical composition according to claim 1, wherein the one or more of the pharmaceutically acceptable acid, the salt thereof, or the mixture thereof comprises citric acid; and the one or more of the pharmaceutically acceptable alkaline earth metal carbonate or hydrocarbonate thereof comprises calcium carbonate.

7. The effervescent solid pharmaceutical composition according to claim 1, wherein a content of an alkaline earth metal is equal to or lower than 300 mg.

8. The effervescent solid pharmaceutical composition according to claim 1, wherein a content of calcium is equal to or lower than 180 mg, and a content of magnesium is equal to or lower than 50 mg.

9. An effervescent solid pharmaceutical composition as defined in claim 1, wherein the composition comprises the active pharmaceutical ingredient in an amount effective for treating a chronic disease; wherein the chronic disease is at least one disease selected from the group consisting of epilepsy; thromboembolic disorders; psychotic disorders; neurodegenerative disorders; allergic disorders; and chronic pain.

10. The effervescent solid pharmaceutical composition according to claim 1, wherein the lacosamide is present in an amount in a range from 2.5 to 10% by weight of the composition.

* * * * *